US010588879B2

(12) United States Patent
McGeer et al.

(10) Patent No.: US 10,588,879 B2
(45) Date of Patent: Mar. 17, 2020

(54) TREATMENT OF AGE-RELATED MACULAR DEGENERATION

(71) Applicant: Aurin Biotech Inc., Vancouver (CA)

(72) Inventors: Patrick L. McGeer, Vancouver (CA); Moonhee Lee, Vancouver (CA)

(73) Assignee: Aurin Biotech Inc., Vancouver (CA)

( * ) Notice: Subject to any disclaimer, the term of this patent is extended or adjusted under 35 U.S.C. 154(b) by 792 days.

(21) Appl. No.: 14/537,611

(22) Filed: Nov. 10, 2014

(65) Prior Publication Data

US 2015/0065573 A1 Mar. 5, 2015

Related U.S. Application Data

(63) Continuation-in-part of application No. 13/541,535, filed on Jul. 3, 2012, which is a continuation-in-part of application No. 13/195,216, filed on Aug. 1, 2011.

(51) Int. Cl.
*A61K 31/194* (2006.01)

(52) U.S. Cl.
CPC .................................. *A61K 31/194* (2013.01)

(58) Field of Classification Search
CPC .................................................. A61K 31/194
See application file for complete search history.

(56) References Cited

U.S. PATENT DOCUMENTS

| | | | |
|---|---|---|---|
| 4,007,270 A | 2/1977 | Bernstein | |
| 4,880,788 A | 11/1989 | Moake | |
| 5,434,185 A | 7/1995 | Collins | |
| 2009/0214538 A1* | 8/2009 | Fung | A61K 39/395 424/135.1 |
| 2013/0035388 A1 | 2/2013 | McGeer | |
| 2013/0035392 A1 | 2/2013 | McGeer | |
| 2014/0163106 A1 | 6/2014 | McGeer | |

FOREIGN PATENT DOCUMENTS

| | | |
|---|---|---|
| CA | 2631071 A1 | 11/2009 |
| WO | 01/57184 A2 | 8/2001 |
| WO | 2007/062186 A2 | 5/2007 |
| WO | 2010/042728 A1 | 4/2010 |

OTHER PUBLICATIONS

Anderson, D.H., et al., "A role for location inflammation in the formation of drusen in the aging eye", Am J Ophthamol, 2002, 134(3):411-431.
Anderson, D.H., et al., "The pivotal role of the complement system in aging and age-related macular degeneration: hypthesis revisited", Prog Ret Eye Res, 2010, 29:95-112.
Benezra, M., et al., "Antiprolifrative activity to vascular smooth muscle cells and receptor binding of heparin-mimicking polyaromatic anionic compounds", Arterioscler Thromb Vasc Biol, 1994, 14:1992-1999.
Cushman, M., et al., "Synthesis of the covalent hydrate of the incorrectly assumed structure of aurintricarboxylic acid", Tetrahedron, 1990, 46(5):1491-1498.
Cushman, M., et al,. "Synthesis and anti-HIV activities of low molecular weight aurintricarboxylic acid fragments and related compounds", J Med Chem, 1991, 34(1):337-342.
Cushman, M., et al., "Structural investigation and anti-HIV activities of high molecular weight ATA polymers", J Org Chem, 1992, 57(26):7241-7248.
Genain, C.P., et al., "Identification of autoantibodies associated with myelin damage in multiple sclerosis", Nat Med, 1999, 5(2):170-175.
Gonzalez, R.G., et al., "Fractionation and structural elucidation of the active components of aurintricarboxylic acid, a potent inhibition of protein nucleic acid interactions", Biochimica et Biophysica Acta, 1979, 562:534-545.
Heisig, G.B., et al., "Ammonium salt of aurin tricarboxylic acid", Organic Syntheses, 1941, 1:54.
Hillmen, P., et al., "The complement inhibitor eculizumab in paroxysmal nocturnal hemoglobinuria", N Engl J Med, 2006, 355(12):1233-1243.
Kira, S., et al., "Nonsense mutation in exon 4 of human complement C9 gene is the major cause of Japanese complement C9 deficiency", Human Gen, 1998, 102(6):605-610.
Lapidus, M., et al., "New inhibitors of complement fixation", Immunopharmacology, 1981, 3:137-145.
Lee, M., et al., "Astrocyctes are GABAergic cells that modulate microglial activity", Glia, 2011, 59(1):152-165.
Lee, M., et al., "Selective inhibition of the membrane attack complex of complement by low molecular weight components of the aurin tricarboxylic acid synthetic complex", Neurobiol Aging, 2012, 33(10):2237-2246.
McGeer, P.L., et al., "Activation of the classical complement pathway in brain tissue of Alzheimer patients", Neuroscience Letters, 1989, 107:341-346.
Okroj, M., et al., "Rheumatoid arthritis and the complement system", Ann Med, 2007, 39(7):517-530.
Owens, M.R., et al., "Aurin tricarboxylic acid inhibits adhesion of platelets to subendothelium", Thrombosis Res, 1996, 81(2):177-185.
Parker, C.J., "Paroxysmal nocturnal hemoglobinuria", Curr Opin Hematol, 2012, 19(3):141-148.
Rogers, J., et al., "Complement activation by b-amyloid in Alzheimer disease", PNAS USA, 1992, 89(21):10016-10020.
Silver, K. L., et al., "Complement driven immune responses to malaria: fuelling severe malarial disease", Cellular Microbiol, 2010, 12(8):1036-1045.
Tan, S., et al., "Oxidative stress induces a form of programmed cell death with characteristics of both apoptosis and necrosis innauronal cells", Journal of Neurochemistry, 1998, 71:95-105.
Wang, Pinglang, et al., "Isolation and structural elucidation of low molecular weight components of aurintricarboxylic acid (ATA)", J Org Chem, 1992, 57(14):3861-3866.

(Continued)

*Primary Examiner* — Kara R McMillian
(74) *Attorney, Agent, or Firm* — Oyen Wiggs Green & Mutala LLP

(57) ABSTRACT

A method of treating age-related macular degeneration. The method includes the step of administering orally or parenterally an effective amount of aurin tricarboxylic acid, aurin quadracarboxylic acid, and/or aurin hexacarboxylic acid, wherein the method excludes administration of components of aurin tricarboxylic acid complex of greater than or equal to 1 kilodalton in molecular weight.

9 Claims, 21 Drawing Sheets

(56) References Cited

OTHER PUBLICATIONS

Yasojima, K., et al., "Generation of C-reactive protein and complement components in atherosclerotic plaques", American J Pathol, 2001, 158(3):1039-1051.

Cushman, M., et al., "Preparation and anti-HIV activities of aurintricarboxylic acid fractions and analogues, direct correlation of antiviral potency with molecular weight", J Med Chem, 1991, 34:329-337.

Ingram et al., "Complement in multiple sclerosis: its role in disease and potential as a biomarker", Clin. Exp. Immunol., 2009, 155(2), pp. 128-139.

* cited by examiner

TREATMENT OF AGE-RELATED MACULAR DEGENERATION

RELATED APPLICATION

This application is a continuation-in-part application of, claims priority to, and incorporates by reference in its entirety, each of U.S. application Ser. No. 13/195,216 filed 1 Aug. 2011 and U.S. application Ser. No. 13/541,535 filed 3 Jul. 2012.

TECHNICAL FIELD

This invention pertains to the use of low molecular weight components of the aurin tricarboxylic acid synthetic complex and their derivatives, to treat human conditions where self-damage is caused by C3 convertase activation of the alternative complement pathway and by membrane attack complex formation resulting from activation of either the alternative or classical pathway, or both. In particular, this invention relates to treatment of age-related macular degeneration.

BACKGROUND

Numerous agents have been described which will inhibit the complement system. These include heparin, suramin, epsilon-aminocaproic acid, and tranexamic acid. However, no orally effective agents have been described that will leave the necessary opsonization of the classical complement pathway functional, but which will prevent self-damage either by blocking C3 convertase activity of the alternative pathway, as well as assembly of the membrane attack complex by both pathways. The only approved agent for treating aberrant complement activation is eculizumab, a humanized monoclonal antibody which blocks C5 conversion of the alternative pathway. It has been approved for the treatment of paroxysmal nocturnal hemoglobinemia. It is effective in 49% of cases (Hillmen et al. 2006). However it does not block the earlier step of C3 convertase, which can result in ongoing hemolysis of erythrocytes (Parker 2012). Moreover, as a high MW immunoglobulin antibody, it will not cross the blood brain barrier and will not be effective in CNS disorders.

The present inventors show in this invention that components of less than 1 kDa MW of the aurin tricarboxylic acid synthetic complex (ATAC) block C3 convertase of the alternative pathway, as well as membrane attack complex (MAC) assembly at the final stage of C9 addition to C5b8 of both the alternative and classical pathways. The present inventors further show that they are safe and effective following oral administration.

Complement is a key component of both the innate and adaptive immune systems. It carries out four major functions: recognition of a target for disposal, opsonization to assist phagocytosis, generation of anaphylatoxins, and direct killing of cells by insertion of the membrane attack complex (MAC) into viable cell surfaces. Although complement is an essential defense system of living organisms, it is widely regarded as a two edged sword. Its opsonizing components are beneficial, but the membrane attack complex is potentially self-damaging.

The complement system as it is understood today is illustrated in FIG. 1. It consists of two main pathways: the classical and the alternative. The pathways have differing opsonizing mechanisms, but they have in common assembly of the terminal components to form the membrane attack complex (C5b-9). The classical pathway commences with the C1q component of the C1 complex recognizing a target that needs to be phagocytosed. Subsequent steps involve dissociation of the C1 complex, cleavage of C2, C4, and C3 to provide amplification as well as covalent attachment of the activated complement components to the target. By this means the target is disposed of by phagocytes that have receptors for the activated complement components so attached.

Both pathways result in C5 being cleaved into C5a and C5b. The released C5b fragment can then insert itself into the membranes of nearby cells. C6, C7, C8 and C9 (n) can then become sequentially attached to the membranes. The addition of C9 renders the complex functional by opening holes in the membranes, thus leading to death of the cells. Its physiological purpose is to kill foreign pathogens, but in the case of sterile lesions, it can destroy host cells by the phenomenon known as bystander lysis.

The complement system therefore operates in two parts. The first part is opsonization, which prepares targeted tissue for phagocytosis. The second part is assembly of the membrane attack complex, which has the purpose of killing cells. The former is essential, but the latter is not. For example, approximately 0.12% of Japanese are homozygous for the nonsense CGA-TGA (arginine 95stop) mutation in exon 4 of C9 (Kira et al., 1999). These individuals cannot make a functioning membrane attack complex. This means that there are more than 150,000 Japanese leading healthy lives despite this deficiency. The Japanese experience indicates that selective inhibition of membrane attack complex formation on a long term basis is a viable therapeutic strategy.

The membrane attack complex exacerbates the pathology in all diseases where there is persistent overactivity of the complement system. In addition, pathology can be exacerbated in diseases in which there is alternative pathway C3 convertase over activity. Such diseases include, but are not limited to, rheumatoid arthritis, paroxysmal nocturnal hemoglobinemia, multiple sclerosis, malaria infection, Alzheimer disease, age-related macular degeneration, and atherosclerosis. The purpose of this invention is to provide a method for successfully treating such conditions. The present inventors screened a large library of organic compounds for any that might have promise of being a selective inhibitor of these pathways. Commercially supplied 'aurin tricarboxylic acid' was the only material to pass the initial screening test. The present inventors found that the product contained only a small amount of aurin tricarboxylic acid. It consisted mostly of a complex of high molecular weight materials. The present inventors fractionated the crude material and investigated the properties of components of less than 1 kDa MW. The desired properties were identified in true aurin tricarboxylic acid (ATA, MW422), aurin quadracarboxylic acid (AQA, MW572), aurin hexacarboxylic acid (AHA, MW858), and their combination which The present inventors term the low molecular weight aurin tricarboxylic acid complex (ATAC).

SUMMARY OF THE INVENTION

This invention is based on properties of components of the aurin tricarboxylic acid synthetic complex of less than 1 kDa (ATAC). For many years it was assumed that aurin tricarboxylic acid was the product obtained by the classical synthetic method, originally described by Heisig and Lauer in 1941 (Heisig and Lauer, 1941), and in U.S. Pat. No. 4,007,270. However, it has been extensively documented since issuance of that patent in 1977 that this standard procedure, and variations of it, produce a complex of compounds, the majority of which are of high molecular weight and are of still uncertain structure (Cushman and Kanamathareddy, 1990; Gonzalez et al., 1979). These high molecular weight components have serious side effects. For example, they bind preferentially with proteins (Cushman et al., 1991), especially those interacting with nucleic acids (Gonzalez et al., 1979). Embodiments of the invention circumvent these overwhelmingly detrimental problems by utilizing molecular weight components of the aurin tricarboxylic acid complex of less than 1 kDa. Embodiments of the invention can be absorbed orally and/or parenterally. Embodiments of the invention act at nanomolar concentrations as selective blockers of the membrane attack complex of complement and/or C3 convertase of the alternative complement pathway.

Embodiments of the invention may be utilized for the treatment of all human conditions where there is chronic activation of the complement system and where it has been shown by autopsy and other types of studies that the membrane attack complex or alternative pathway activation exacerbates the lesions. These conditions include, but are not limited to, rheumatoid arthritis, paroxysmal nocturnal hemoglobinemia, multiple sclerosis, malaria infection, Alzheimer disease, age-related macular degeneration, atherosclerosis and atypical hemolytic uremic syndrome.

In 1977, U.S. Pat. No. 4,007,270 was issued for "Complement Inhibitors" which included the term 'aurin tricarboxylic acid'. But the patent failed to show the true chemical nature of the material upon which the claims were based. There was no chemical or structural analysis of the patentee's synthetic product. Those skilled in the art would have concluded, based on subsequent publications that the 'aurin tricarboxylic acid', as described in that patent, was not the material claimed, and would therefore not be useful in the applications described. Firstly, they would have been taught, on the basis of molecular analyses conducted subsequently to issuance of U.S. Pat. No. 4,007,270, that the product, as produced by the synthetic method described in the patent, would not be aurin tricarboxylic acid, but would consist mostly of a mixture of high molecular weight materials of uncertain structure (e.g. Gonzalez et al., 1978, Kushman and Kanamatharedy, 1990). They would further have been taught that these components have powerful side effects which would render them unsuitable for human administration, including inhibition of protein nucleic acid interactions (Gonzales et al., 1979), and inhibition of adhesion of platelets to endothelium (Owens and Holme, 1996). They would also have been taught that the proposed mechanism of action was against the opsonizing components of complement as shown by the described effects on C1 inhibitor (Test Code 026) and not a specific inhibitor of the membrane attack complex, or of C3 convertase. Therefore, by inhibiting the essential function of classical pathway opsonization, the material would have been unsuitable for chronic administration. They would also have known from subsequent teaching that oral administration would be ineffective since the material was of too high molecular weight to be absorbed from the digestive tract or to be able to reach the brain.

The crude material as the starting point for this invention can be obtained by synthesis using the method of Cushman and Kanamathareddy (Cushman and Kanamathareddy, 1990). It can also be prepared from commercial sources, such as the triammonium salt of the aurin tricarboxylic acid complex known as Aluminon, or as 'aurin tricarboxylic acid' from suppliers such as Sigma-Aldrich. The sources and methods of synthesis of these products have not been publicly described.

More than 85% of the powder the present inventors synthesized, or equivalent powder obtained from commercial sources including Aluminon, is a mixture of high molecular weight polymeric products. The exact structures of these products are as yet uncertain (Gonzales et al., 1979; Cushman and Kanamathareddy, 1990; Cushman et al., 1992).

The powder the present inventors obtained from synthesis, or commercially purchased 'aurin tricarboxylic acid' from Sigma-Aldrich, or from Aluminon, was separated into high and low molecular weight components by passing through 1 kDa and 0.5 kDa MW filters. The low MW components were separated and analyzed by mass spectroscopy. Results from the three sources were almost identical. The low MW components made up only 12-16% of the total. They all contained three molecules of MW 422, 572, and 858. These MWs correspond to structures with three, four and six salicylic acid moieties. The present inventors refer to these as aurin tricarboxylic acid (ATA), aurin quadracarboxylic acid (AQA) and aurin hexacarboxylic acid (AHA) (FIG. 2). They were in a rough proportion of 78% ATA, 15% AQA and 7% AHA, or approximately 11%, 2%, and 1% of the crude starting material. This mixture is referred to as the aurin tricarboxylic acid complex (ATAC).

The present inventors show in this invention that components of the aurin tricarboxylic acid less than 1 kDa, in particular AHA, AQA and/or ATA, selectively block the addition of C9 to C5b-8 so that the MAC cannot form. The present inventors also show that these molecules inhibit C3 convertase of the alternative pathway by binding to Factor D in serum. These molecules inhibit hemolysis of human, rat, and mouse red cells with an $IC_{50}$ in the nanomolar range. When given orally to Alzheimer disease type B6SJL-Tg mice, they inhibit MAC formation in serum and improve memory retention. On autopsy, mice fed with these materials, or administered to them parenterally, show no evidence of harm to any organ. These molecules have also demonstrated improvement of symptoms in patients with age-related macular degeneration and efficacy against atypical hemolytic uremic syndrome. The present inventors conclude that this invention may be effective in the therapy of a spectrum of human disorders where self-damage from the MAC or alternative pathway activation occurs.

BRIEF DESCRIPTION OF DRAWINGS

The following drawings show non-limiting embodiments of the invention.

FIG. 2A shows ATA, MW 422 (5,5'-((3-carboxy-4-oxocyclohexa-2,5-dienn-1-ylidene)methylene)bis(2-hydroxybenzoic acid). FIG. 2B shows AQA, MW 572 (putative structure 5,5,4(3-carboxy-5-((3carboxy-4-oxocyclohexa-2,5-dien-1-ylidene)methyl)-4-hydroxyphenyl)methylene)bis(2-hydroxybenzoic acid)).

FIG. 2C shows AHA, MW858 (putative structure, 5,5'-((3-carboxy-5-((3-carboxy-4-oxocyclohexa-2,5-dien-1-ylidene)methyl)-4-hydroxybenzyl)-4-hydroxyphenyl)methylene)bis(2-hydroxybenzoic acid)). ES− means negative scan mode, giving values of −1 to the true mass. ES+ mean positive scan mode giving values of +1 to the true mass.

FIG. 3A shows human serum results with nearly identical $IC_{50}$ values as follows: ATA 544 nM, for AQA 576 nM, for AHA 559 nM and for ATAC 580 nM. FIG. 3B shows rat serum results with an $IC_{50}$ for ATAC of 268 nM.

FIG. 4A: Western blots of membranes developed with antibodies to C1q, C3, C4 and C5. Lane 1, untreated serum; lane 2, serum with red blood cells added; lane 3 serum with red blood cells protected with ATAC. Notice that in untreated serum, bands for C1q, C3, C4, and C5 were readily detected. In lanes 2 and 3, the activated products C3d, C4d, and C5a were detected indicating opsonization had taken place. In lane 2, the MAC was detected, but not in lane 3, indicating that ATAC was blocking MAC formation. To analyze which step in MAC formation was involved, western blot membranes were treated with antibodies to C6, C7, C8, and C9 for ATAC (FIG. 4B), ATA (FIG. 4C), AQA (FIG. 4D), and AHA (FIG. 4E). The results are identical. In each panel, lane 1 is serum, lane 2 is unprotected red blood cells, lane 3 is red blood cells protected with either ATA, AQA, AHA, or ATAC, and lane 4 is the same as lane 3 but with C9 protein supplementation. It shows that C6, C7, C8 and C9 are readily detected in untreated serum. Lane 2 shows that, in unprotected red blood cells that have become hemolysed by complement attack, only C5b-9, the fully formed membrane attack complex, is detected. Lane 3, in which the cells have been protected either by ATA, AQA, AHA or ATAC, the membrane attack complex does not fully form but becomes arrested at the C8 stage. The C6 antibody detects C5b6, C5b67, and C5b678. The C7 antibody detects C5b67 and C5b678, while the C8 antibody detects C5b678. Lane 4 provides confirmation that the blockade occurs only at the C9 stage. It can be seen that C5b-9 is now detected upon probing with C6, C7, C8 and C9, thus establishing that the ATAC block was at the C9 stage. A very faint C9 band is still visible in the blots indicating that not all the added C9 was consumed in the process.

FIG. 5A: Normal serum demonstrates detectable bands for properdin, C3, Factor B and Factor D (lane1). Upon activation with zymosan in the presence of C1 inhibitor, bands corresponding to PC3b, PC3bBb and PC3bBbC3b appear on blots developed with properdin and C3b antibodies, and PC3bBb and PC3bBb and PC3bBbC3b on the one developed with Factor Bb antibody (lane 2). These data demonstrate that properdin is required for C3b binding to initiate the alternative pathway, and that C3 and C5 convertases are activated. The addition of ATA results in bands appearing only for PC3b and PC3bB, indicating a block at the stage of Factor D cleavage of bound Factor B (lane 3). Lane 4 where properdin is added, and lane 5 where Factor D is added, both show reappearance of weak bands for PC3bBb and PC3bBbC3b, indicating partial recovery of alternative pathway activation. No bands for Factor D were detected on the erythrocyte membranes, indicating that this protease did not become bound but remained in solution. Three independent experiments were performed and these are representative. FIG. 5B: Western blots of the residual serum developed with the antibody to C5/C5a. A band for C5 was readily detected in normal serum (lane 1). Treatment with zymosan and C1 inhibitor resulted in disappearance of the C5 band and appearance of the activation product C5a (lane 2). The addition of ATA and C1 inhibitor (lane 3) prevented cleavage of C5, which was partially antagonized by treatment with properdin (1 microgm/mL, lane 4) and Factor D (0.1 microgm/mL, lane 5). FIG. 5C: Treatment of the residual membranes with antibodies to C5/C5b, C6, C7, C8 and C9. Lane 1 of normal serum shows that each complement protein was detected in normal serum. Lane 2 of membranes following serum treatment with zymosan and C1 inhibitor resulted in disappearance of each of the protein bands and appearance of the MAC formation components C5b6, C5b67, C5b678, and the fully formed C5b-9. Lane 3 in which ATA was added shows that complete blockade appeared with no activation bands appearing on the membranes. Lanes 4 and 5, where the serum was supplemented with properdin and Factor D respectively, showed partial activation of the complement system with weaker bands for C5b6, C5b67, and C5b678 appearing, but there was still blockade at the C5b-9 stage indicating that ATA was also blocking the addition of C9 to C5b-8.

DESCRIPTION

Figure 1:
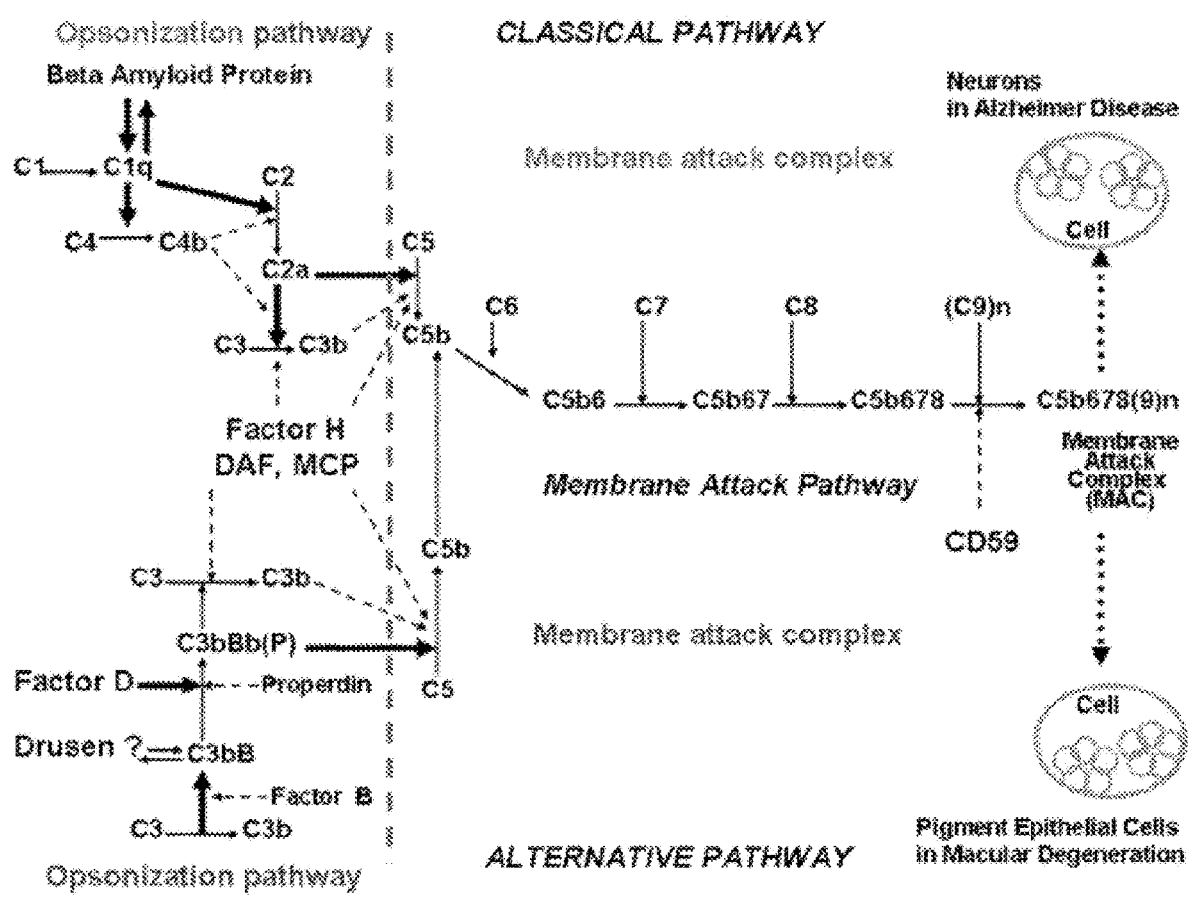
FIG. 1. Shows a standard schematic representation of the classical complement pathway as activated in Alzheimer disease, and the alternative complement pathway as activated in age-related macular degeneration. Notice that assembly of the membrane attack complex is common to both the classical and alternative pathways.
Figure 2A:
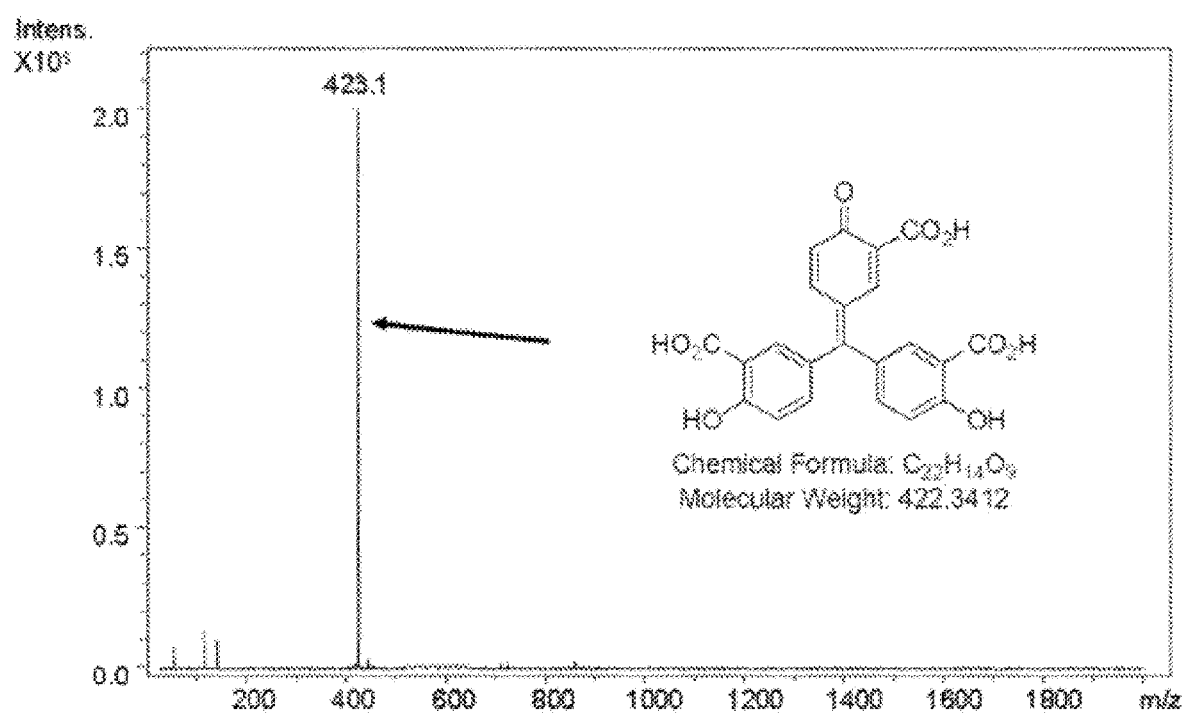
FIG. 2A to 2C show the putative structure and mass of the three components of the aurin tricarboxylic acid synthetic complex (ATAC) of less than 1 KDa with corresponding mass-spec analyses of the separated components.
Figure 2B:
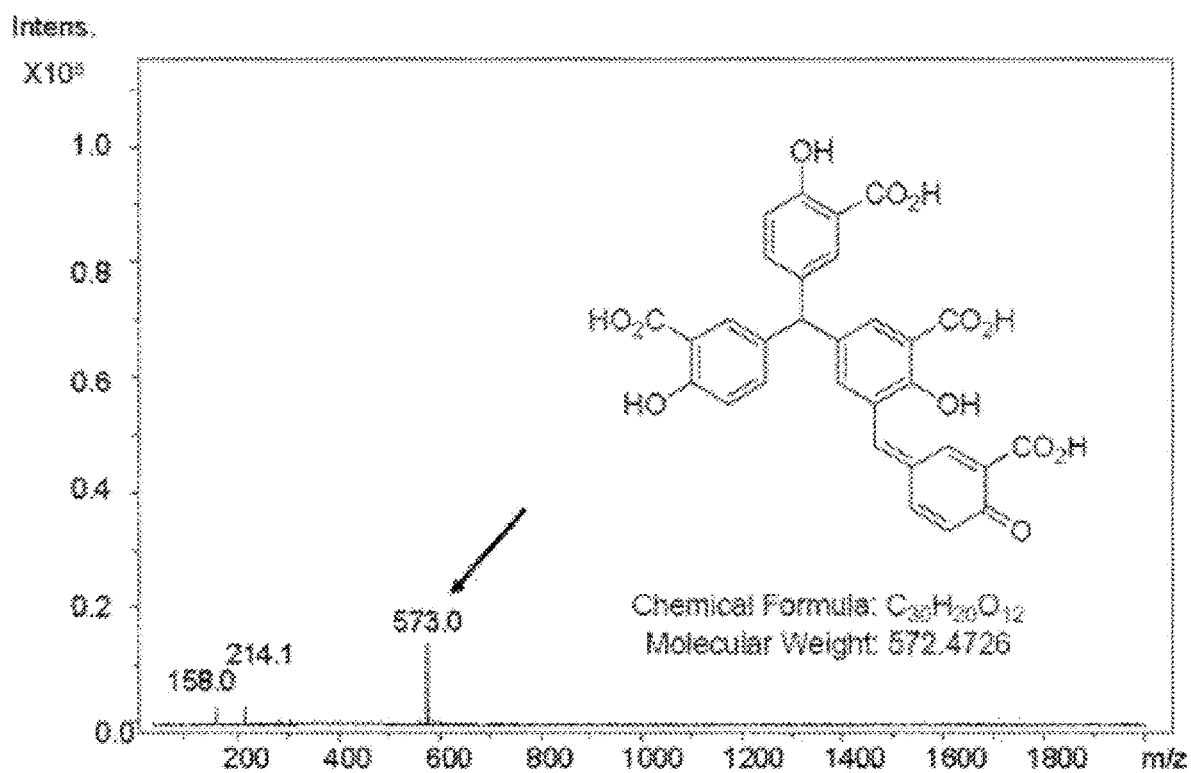
Figure 2C:
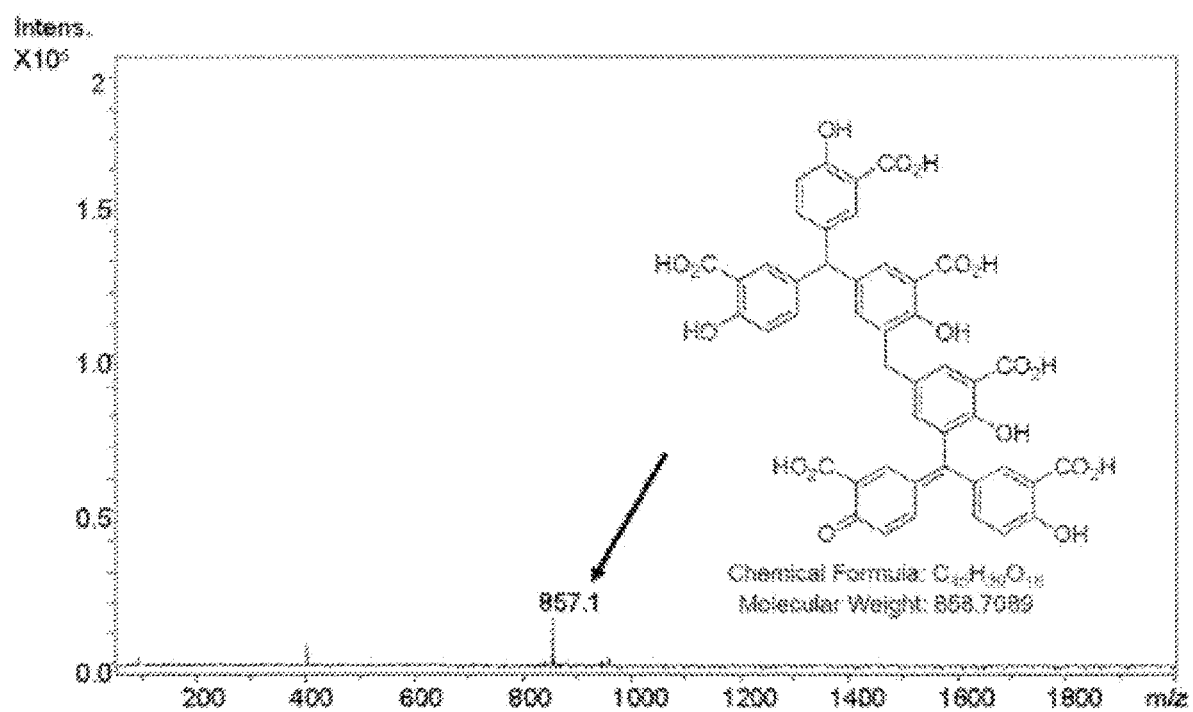

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Synthesis of the aurin tricarboxylic acid complex was carried out according to the published standard procedure (Cushman and Kanamathareddy, 1990).

1. Synthesis of 3,3'-dichloro-5,5'-dicarboxy-4,4'-dihydroxydiphenylmethane

3-Chlorosalicylic acid (1 g) was dissolved in methanol (10 mL). Water (2.5 mL) was added and the flask was cooled to −5° C. in an ice-salt (NaCl) bath. Concentrated sulfuric acid (30 mL) was slowly added over 20 min with the temperature being maintained at −5° C. The reaction mixture was then stirred at this temperature for 1 h while a solution of 37% formaldehyde (4 mL) was added. The temperature was maintained at 0° C. for 1 h and then the mixture was left at room temperature for a further 24 h. The reaction mixture was poured into crushed ice (150 g) and the precipitate filtered and dried to give the product, 3,3'-dichloro-5,5'-dicarboxy-4,4'-dihydroxydiphenylmethane (yield 0.92 g, 92%) as a powder. The sample was recrystallized from methanol.

2. Synthesis of 3,3'-dicarboxy-4,4'-dihydroxydiphenylmethane 3,3'-Dichloro-5,5'-dicarboxy-4,4'-dihydroxydiphenylmethane (0.92 g) was dissolved in ethanol (18 mL) and triethylamine (10 mL). Palladium on carbon was added to the solution and the mixture was stirred under an atmosphere of hydrogen for 48 h. The catalyst was filtered off, the solvent evaporated, and water (100 mL) added to the residue. The solution was cooled, and concentrated hydrochloric acid (5 mL) added. The white precipitate was filtered and dried to give the product, 3,3'-dicarboxy-4,4'-dihydroxydiphenylmethane (0.75 g, 90%) as a solid. It was dissolved and recrystallized from methanol.

3. 3,3',3"-tricarboxy-4,4,4"-trihydroxpriphenylcarbinol Complex (Aurin Tricarboxylic Acid Complex)

Powdered sodium nitrite (4 g) was added with vigorous stifling to concentrated sulfuric acid (4 mL). A mixture of the compound 3,3'-Dicarboxy-4,4'-dihydroxydiphenylmethane (0.75 g) and salicylic acid (0.38 g) was stirred until it was homogeneous. It was then poured into the solution of sodium nitrite-sulfuric acid. Stirring was continued at room temperature for an additional 18 h. The mixture was poured into crushed ice (100 g) with stifling. The dark orange precipitate was filtered and dried to give the crude product (0.6 g, yield 60%). The powder was dissolved in 2% ammonium hydroxide for analysis.

Separation and Analysis of ATAC

Figure 3A:
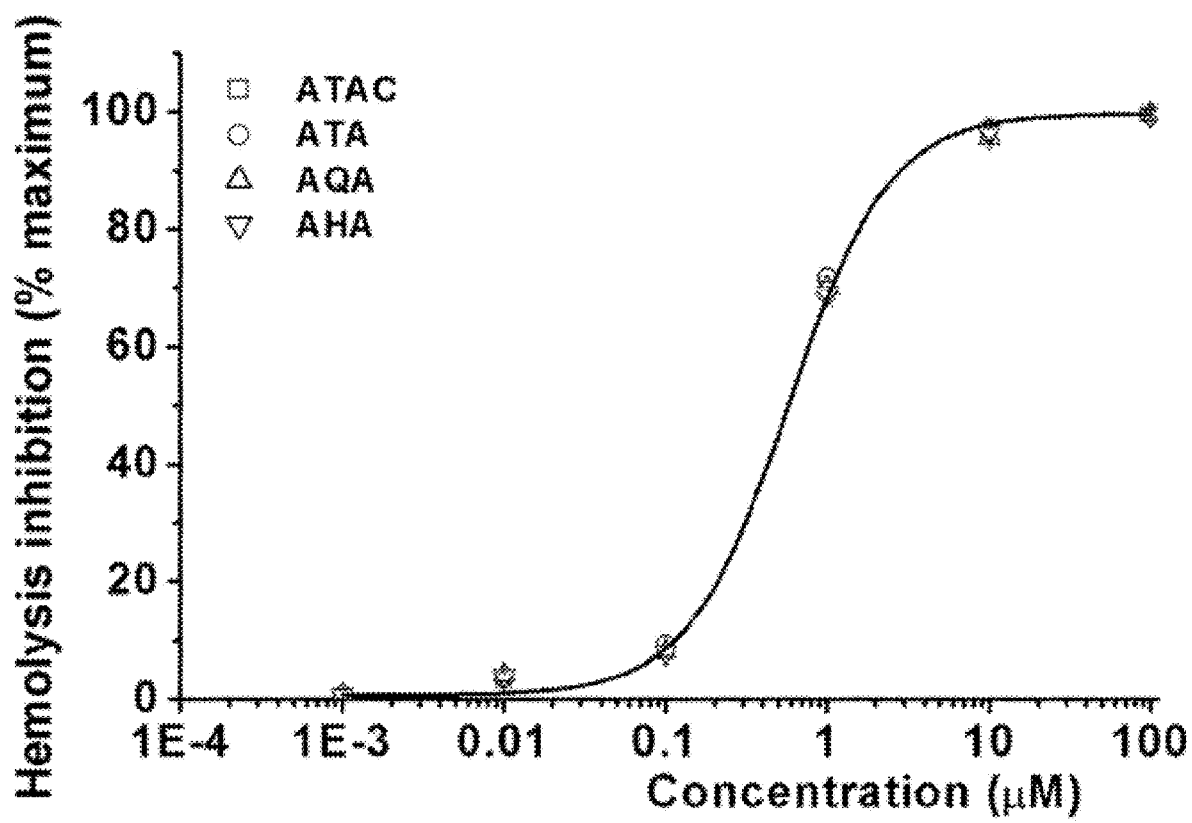
FIGS. 3A and 3B show CH50 analyses of serum.
Figure 3B:
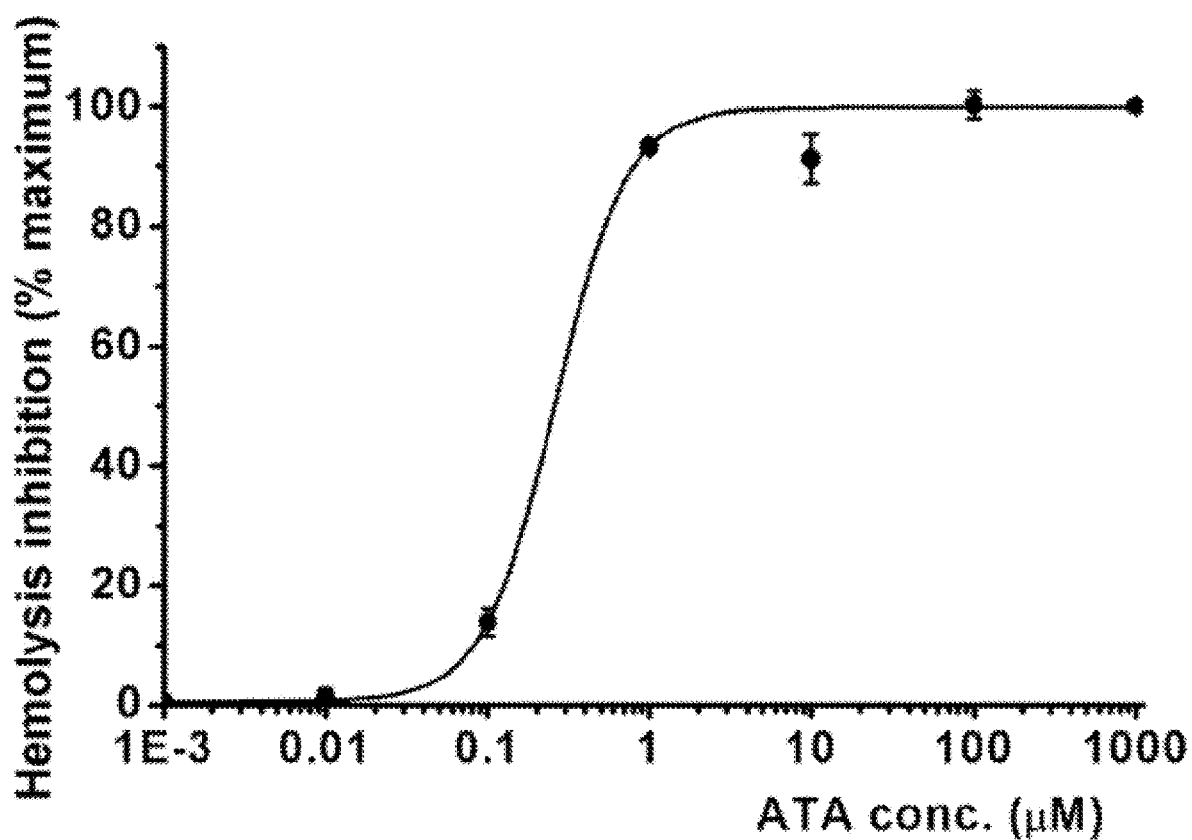

The powder the present inventors obtained from synthesis, or commercially purchased 'aurin tricarboxylic acid' from Sigma-Aldrich, or Aluminon from GFS Chemicals Inc. (Columbus, Ohio) were separated into high and low molecular weight components. In a typical experiment, five grams of material were dissolved in 0.2% ammonium hydroxide (45 mL) and forced through a 1 kDa filter (PLAC04310, Millipore, Ballerica, Mass.) under air pressure (70-75 psi, 5.3 kg/cm$^2$ for 6 h). The filtered material was recrystallized by lyophilization. The filtrate (4.5 mg in 1 mL) was then loaded onto a size exclusion chromatography column (Sephadex LH-20 packed in 60% ethanol, GE Healthcare, Piscataway, N.J.). Three different eluent fractions were collected. The three fractions, as well as the starting mixture, were analyzed by mass spectrometry on a Waters ZQ apparatus equipped with an ESCI ion source and a Waters Alliance Quadrupole detector. All samples were exposed to electron spray ionization in positive and negative modes, as well as atmospheric pressure chemical ionization. Scans ranged from m/z 0-1100 and m/z 500-1500. Three molecules were detected of MW 422, 572, and 858. These molecular weights correspond to ATA, AQA, and AHA respectively as shown in FIG. 3. There was no other derivative of less than 1.5 kDa detected. The components were separated and analyzed by mass spectroscopy. Results from the three sources were almost identical. The low MW components made up only 12-16% of the total. They all contained three molecules of MW 422, 572, and 858.

Evaluation of the Low Molecular Weight Products as Selective Inhibitors of the Membrane Attack Complex and C3 Convertase To evaluate the strength of blockade of the classical complement pathway by the low molecular weight products of the aurin tricarboxylic acid complex, (i.e. ATA plus AQA plus AHA), the standard CH50 assay was employed. Sheep red blood cells were sensitized by incubation overnight with rabbit anti sheep red blood cell antibody. Then dilutions of serum, with and without various amounts of the low molecular weight aurin tricarboxylic acid fraction (ATAC), were incubated with the sensitized red blood cells for 1 hour at 37° C. The incubates were centrifuged at 5,000 rpm for 10 min. The hemoglobin released into the serum from red blood cells that had been destroyed by complement attack, was determined by reading the optical density (OD) at 405 nm. As a positive control, red blood cells were 100% lysed with water, and as a negative control, no serum was added to the incubate.

The results are shown in FIG. 3. Each of these components inhibited human complement-mediated red blood cell hemolysis almost identically. IC50 values were for ATA 544 nM, for AQA 576 nM, for AHA 559 nM and for ATAC 580 nM. The IC50 for ATAC in rat serum was 268 nM. These data establish that inhibition of complement activation by low molecular weight aurin tricarboxylic acid derivatives is in the nanomolar range and includes rodent as well as human serum.

To determine at which stage of the complement cascade blockade was occurring, a variation of the CH50 assay was carried out. Instead of measuring hemolysis, western blot analyses were run to determine which serum complement proteins were consumed and converted into activated complement products on susceptible membranes. Complement proteins are consumed and converted only up to the stage of blockade. At stages beyond the blockade, they remain unchanged in the serum but their activated products appear on cell membranes. Results are shown in FIG. 4. Human serum was diluted 16 fold. It was then treated for 30 min with ATA, AQA, AHA or ATAC. Then antibody-conjugated sheep red blood cells in an equal volume were added. The mixtures were incubated at 37° C. for 1 h. They were then treated with a lysis buffer followed by a loading buffer for western blots. Equal amounts of protein from each sample were loaded onto gels and separated by 10% SDS-PAGE. Following SDS-PAGE, proteins were transferred to a PVDF membrane. The membranes were then treated with various primary antibodies followed by labeled secondary antibodies using well established techniques (Lee et al., 2011). The list of antibodies that were utilized is shown in Table 1. Bands recognized by the antibodies were visualized by use of an enhanced chemiluminescence system and exposure to photographic film. For probing the same membrane with different antibodies, the membranes were treated with stripping buffer (Lee et al., 2011) and then treated as before with a different primary antibody.

TABLE 1

Antibodies and peptides used for experiments

| Antibodies and proteins | Company | Dilution/final concentration |
|---|---|---|
| Polyclonal goat anti-sera to Human C1q | Quidel, San Diego, CA | 1/2,000 for blotting (FIG. 4) |
| Monclonal mouse anti C3b Ab | Quidel, San Diego, CA | 1/2,000 for blotting (FIG. 5) |
| Monoclonal mouse anti C3d Ab | Quidel, San Diego, CA | 1/2,000 for blotting (FIG. 4) |
| Monoclonal mouse anti C4d Ab | Quidel, San Diego, CA | 1/2,000 for blotting (FIG. 4) |
| Monoclonal mouse anti C5/C5a Ab | Abcam, Cambridge, MA | 1/2,000 for blotting (FIGS. 4 and 5) |
| Monoclonal mouse anti C5/C5b Ab | Abcam, Cambridge, MA | 1/2,000 for blotting (FIG. 5) |
| Polyclonal Goat anti C6 Ab | Quidel, San Diego, CA | 1/2,000 for blotting (FIGS. 4 and 5) |
| Polyclonal Goat anti C7 Ab | Quidel, San Diego, CA | 1/2,000 for blotting (FIGS. 4 and 5) |
| Polyclonal Goat anti C8 Ab | Quidel, San Diego, CA | 1/2,000 for blotting (FIGS. 4 and 5) |
| Polyclonal Goat anti C9 Ab | Quidel, San Diego, CA | 1/2,000 for blotting (FIGS. 4 and 5) |
| Monoclonal mouse anti properdin Ab | Quidel, San Diego, CA | 1/2,000 for blotting (FIG. 5) |
| Monoclonal Factor Bb Ab | Quidel, San Diego, CA | 1/2,000 for blotting (FIG. 5) |
| Monoclonal Factor D Ab | Abcam, Cambridge, MA | 1/2,000 for blotting (FIG. 5) |
| Human properdin protein | Quidel, San Diego, CA | 1 ug/ml (FIG. 5) and 32 ng/ml (FIG. 6) |
| Human Factor D Protein | Quidel, San Diego, CA | 1 ug/ml (FIG. 5) and 32 ng/ml (FIG. 6) |
| Human Factor B Protein | Sigma, St. Louis, MO | 32 ng/ml (FIG. 6) |
| Human C2 Protein | Sino Biologicals Inc., Beijing, China | 32 ng/ml (FIG. 6) |
| Human C3 Protein | Sigma, St. Louis, MO | 32 ng/ml (FIG. 6) |
| Human C4 Protein | Complement technology Inc., Tyler, TX | 32 ng/ml (FIG. 6) |
| Human C5 Protein | Complement technology Inc., Tyler, TX | 32 ng/ml (FIG. 6) |
| Human C6 Protein | Sigma, St. Louis, MO | 32 ng/ml (FIG. 6) |
| Human C7 Protein | Quidel, San Diego, CA | 32 ng/ml (FIG. 6) |
| Human C8 Protein | Sigma, St. Louis, MO | 32 ng/ml (FIG. 6) |
| Human C9 Protein | Sigma, St. Louis, MO | 1 ug/ml (FIG. 4) and 32 ng/ml (FIG. 6) |
| C1 inhibitor | Quidel, San Diego, CA | 1.8 ug/ml (1/100 dilution) (FIG. 5) |

Figure 4A:
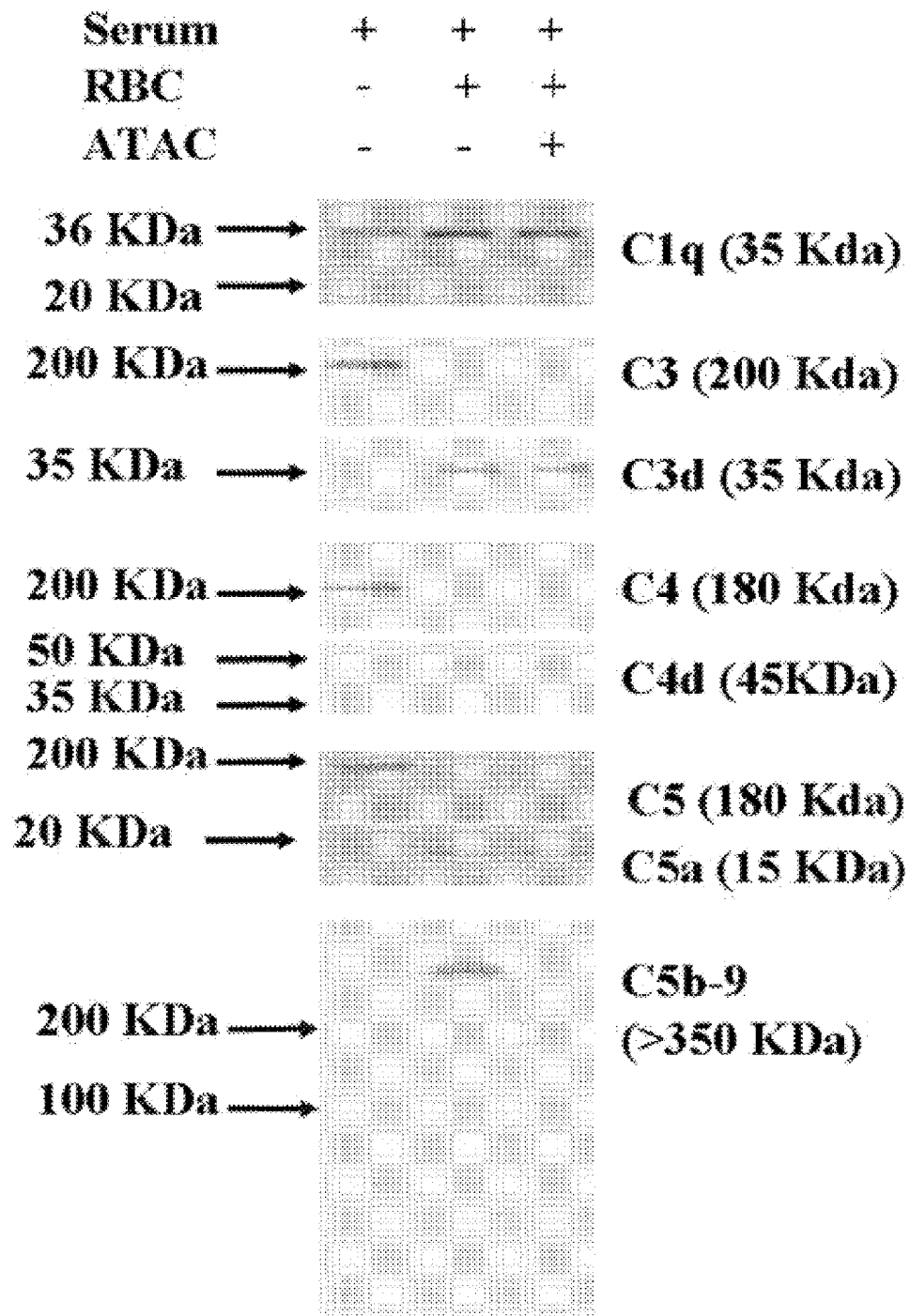
FIG. 4A to 4E show Western blot analyses demonstrating that ATA, AQA, AHA, and ATAC act selectively by blocking the addition of C9 to C5b678 thus preventing formation of the membrane attack complex. Normal human serum was pre-treated with aliquots of aqueous solutions of ATA, AQA, AHA and ATAC prior to adding sheep red blood cells sensitized to human complement. The reaction mixtures were incubated at 37° C. for 1 h. Aliquots were loaded on 10% polyacrylamide gels and subjected to SDS-PAGE. Proteins were transferred to membranes and developed with appropriate primary antibodies to complement proteins (Table 1)

Typical results are shown in FIG. 4A. The left lane was loaded with serum only and shows that bands for C1q, C3, C4, and C5 were readily detected. The adjacent lane illustrates the effect of adding sensitized red blood cells, which then become hemolyzed by complement attack. Native serum proteins are consumed and become incorporated into the red cell membranes. C1q was not metabolized, but the band was intensified due to its dissociation from the C1 complex. Native C3 was no longer detected because it had been cleaved, and the C3b fragment had become covalently attached to the membrane. The degradation product C3d was detected. C4 was no longer detected because it had similarly been cleaved and the C4b fragment attached to the membrane and metabolized into the degradation product C4d. This fragment was also detected. C5 was cleaved and a band for the C5a product detected. Finally, the C5b-9 membrane attack complex, which had formed on the red cell membrane causing its hemolysis, was detected.

The next membrane shows the effect of incubation of serum plus sensitized red blood cells in the presence of the ATAC. Identical bands for the opsonization steps were detected, but the red cells were not hemolyzed and the membrane attack complex was not detected.

Figure 4B:
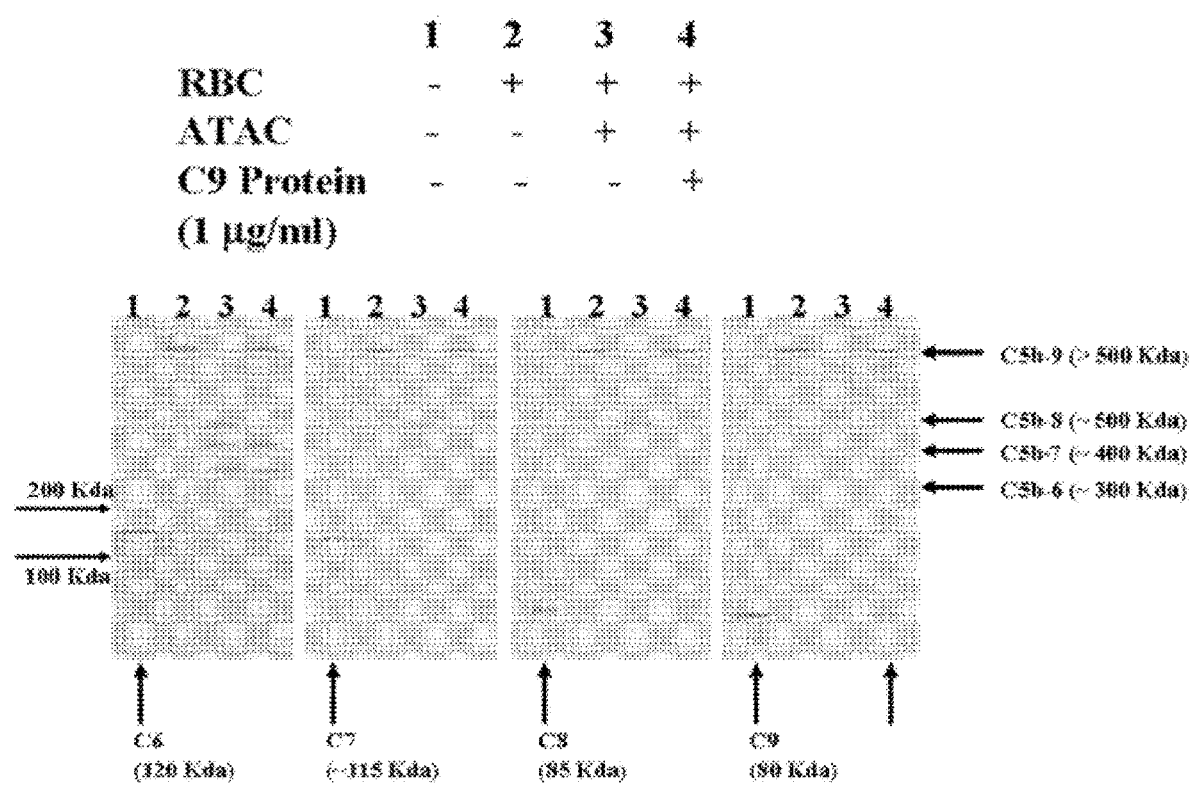
Figure 4C:
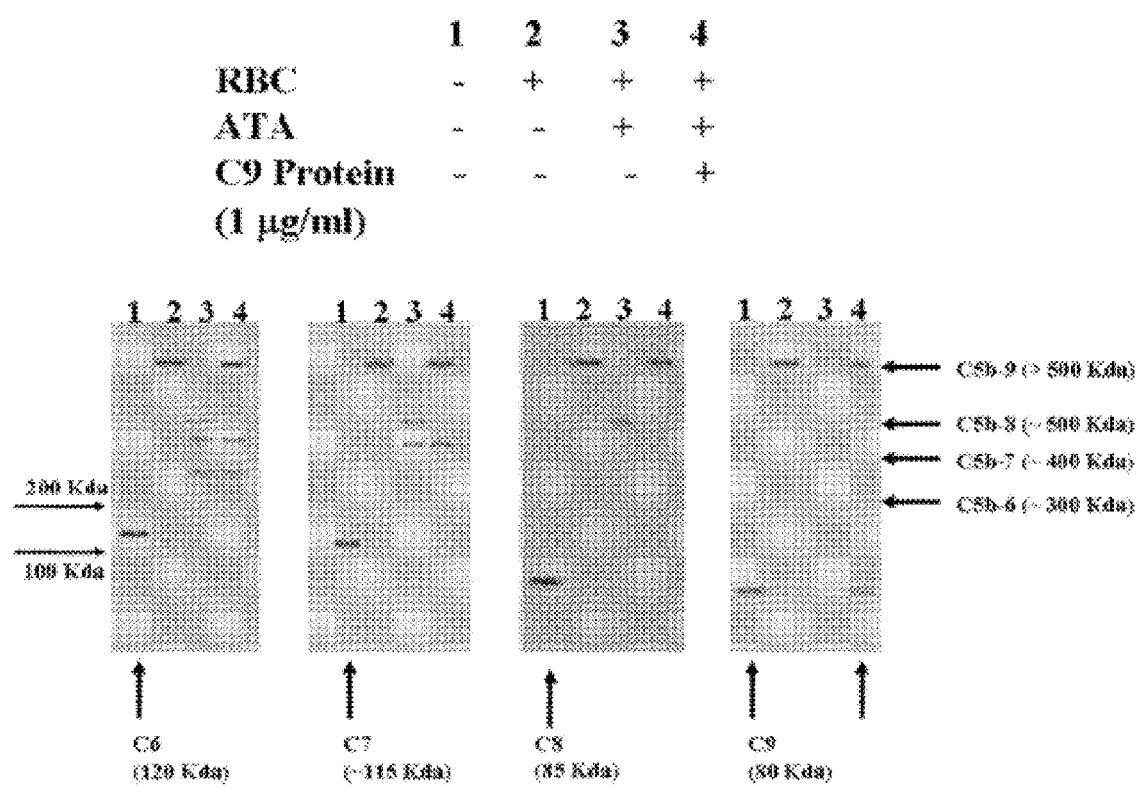
Figure 4D:
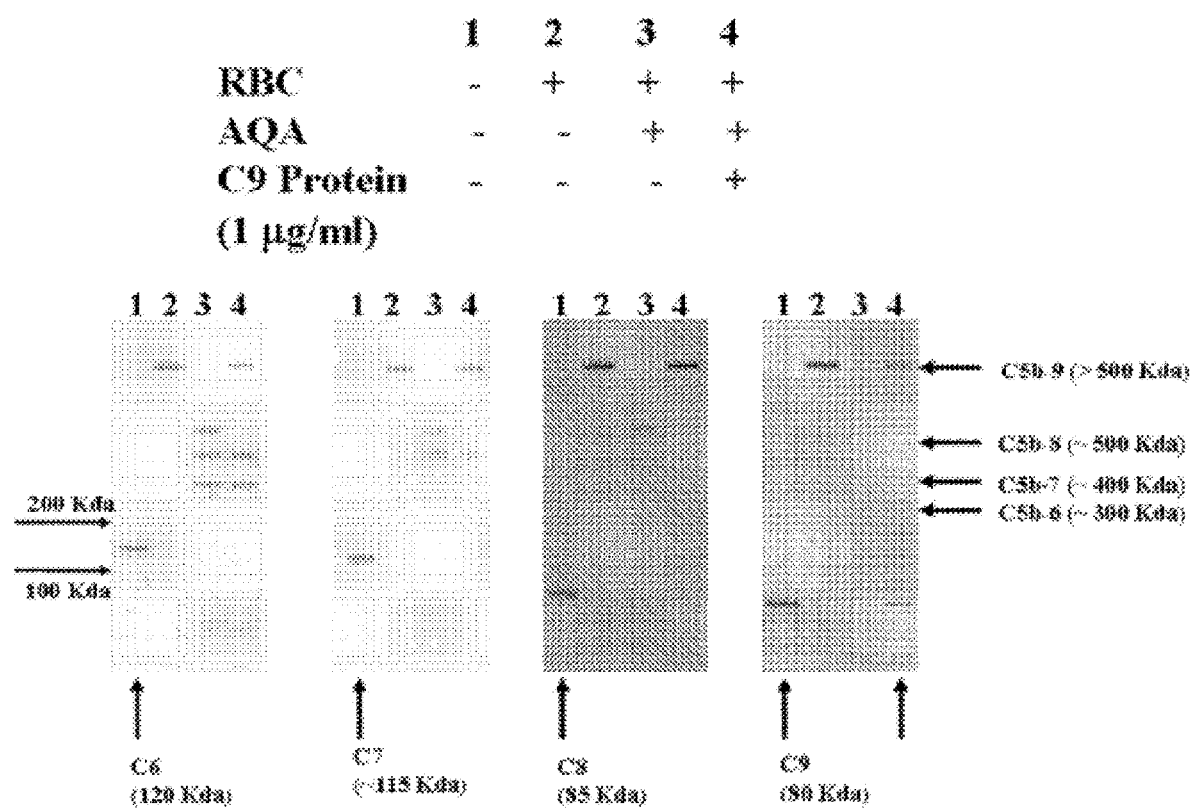
Figure 4E:
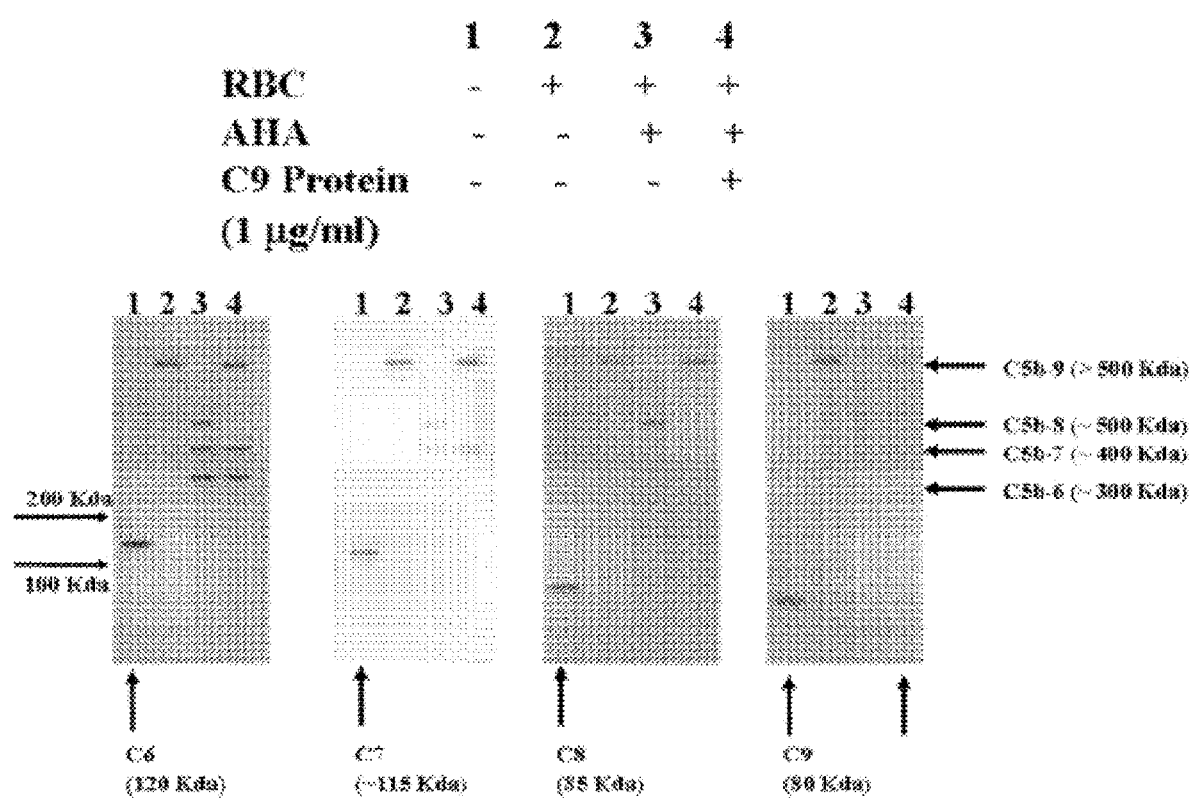

To determine at which stage of assembly of the membrane attack complex was being blocked, additional analyses were carried. The incubations were the same as before except that the red blood cells were separated from the residual serum and washed prior to being treated for western blot analysis. The blots were probed with antibodies to C6, C7, C8 and C9. The results are shown in FIG. 4b for ATAC, 4c for ATA, for 4d for AQA and 4e for AHA. The results were identical for each component. Lane 1 for human serum alone shows that C6, C7, C8 and C9 were readily detected in the untreated serum. Lane 2 shows that in unprotected red blood cells that have become hemolyzed by complement attack, these antibodies detected only C5b-9, the fully formed membrane attack complex. Lane 3, in which the cells have been protected by ATAC, shows that the membrane attack complex does not fully form but becomes arrested at the C8 stage. The C6 antibody detected C5b6, C5b67, and C5b678. The C7 antibody detected C5b67 and C5b678, while the C8 antibody detected C5b678. These data establish that ATAC arrests formation of the membrane attack complex at the stage where C9 attaches to C5b678. Since C9(n) is required for creating the membrane destroying holes, this blockade is highly specific to preventing C9 attachment.

To determine the effects of ATAC on the alternative pathway, experiments were carried out where the classical pathway was blocked with C1 inhibitor (1.8 micrograms/mL) or with a C4b antibody (1,1000 dilution). For these experiments, human serum (15-fold dilution) was incubated with C1 inhibitor and ATA (5 microM, lane 3), or ATA with either properdin (1 microgm/mL, lane 4) or Factor D (0.1 microgm/mL, lane 5) for 1 h before opsonized zymosan (1 microgm/mL) was added. The mixtures were incubated for 1 h at 37° C. and centrifuged at 5,000 rpm for 10 min. The pellets were washed two times with Hank's balanced salt solution (HBSS) and treated with sample loading buffer for SDS-PAGE and immunoblotting. The buffer consisted of 50 mM Tris (pH 6.8), 0.1% SDS, 0.1% bromophenol blue and 10% glycerol. To preserve the molecular complexes that had formed, mild conditions for SDS-PAGE were followed. For C1q blotting, conventional sample loading buffer (50 mM Tris (pH 6.8), 1% SDS, 0.1% bromophenol blue and 10% glycerol and 2% beta-mercaptoethanol) was used.

Figure 5A:
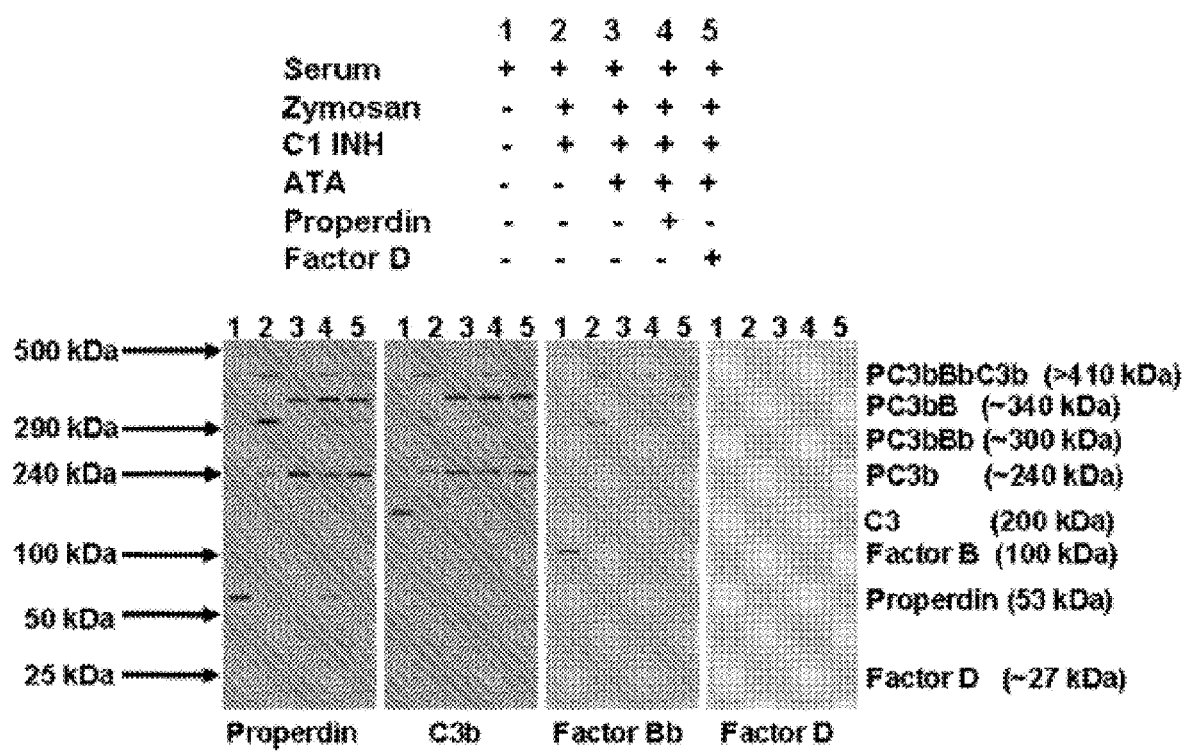
FIG. 5A to 5C show western blots of membranes developed with antibodies to properdin, C3/C3b, Factor B/Bb and Factor D, demonstrating the effect of inhibiting classical pathway activation with C1 inhibitor or C4b antibody, and showing inhibition of C3 convertase by ATA.

FIG. 5A shows the results when western blots of these erythrocyte membranes were developed with monoclonal antibodies to properdin (1/2,000), C3b (1/2,000), Factor B/Bb (1/2,000) and Factor D (1/2,000) respectively. Lane 1 in each blot shows that the native proteins were detected in untreated serum. Lane 2 shows that, in red blood cells that have become hemolyzed by complement attack mediated by zymosan in the presence of CI inhibitor, similar bands were detected by antibodies to properdin, C3b and Factor B/Bb corresponding in MW to PC3b (~240 kDa), PC3bB (~340 kDa), PC3bBb (~300 kDa) and PC3bBbC3b (>410 kDa). These data show that C3 convertase and C5 convertase were present on the membranes. However an independent band for C3b was not detected. This result indicates that C3b required properdin to bind and direct its binding to the erythrocyte membranes. The antibody to Factor D did not detect any bands for Factor D, indicating that Factor D did not form any SDS stable complexes on the membranes. Lane 3 shows the results obtained in the presence of 5 microM ATA. Bands for PC3bBb and PC3bBbC3b did not form. Instead, strong bands for the earlier steps of PC3b and PC3bB appeared. These results indicate that arrest of activation occurred at the stage where PC3bB becomes cleaved by Factor D to form the C3 convertase enzyme. Lanes 4 and 5 illustrate the effect of supplementing the serum with properdin (1 microgm/mL) or Factor D (0.1 microgm/mL). The effect of ATA was partially overcome. Weak bands for PC3bBb and PC3bBbC3b reappeared, although the band for PC3bB persisted. No bands Factor D were observed. This result provides further evidence that Factor D does not form a stable bond attached to membranes but remains in the serum.

Figure 5B:
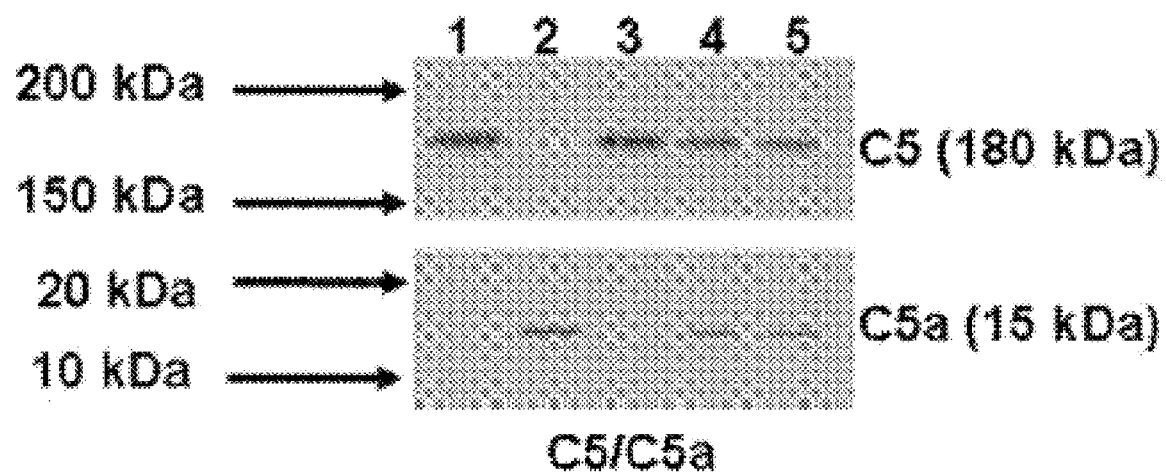

FIG. 5B illustrates the effects on the residual serum as shown by western blots developed with an antibody to C5/C5a. Treatment with zymosan and C1 inhibitor resulted in disappearance of the C5 band and appearance of the activation product C5a (lane 2). The addition of ATA and C1 inhibitor (lane 3) prevented cleavage of C5, which was partially antagonized by treatment with properdin (lane 4) and Factor D (lane 5). Weaker bands for C5 appeared as well as faint bands for C5a indicating partial activation of serum C5.

Figure 5C:
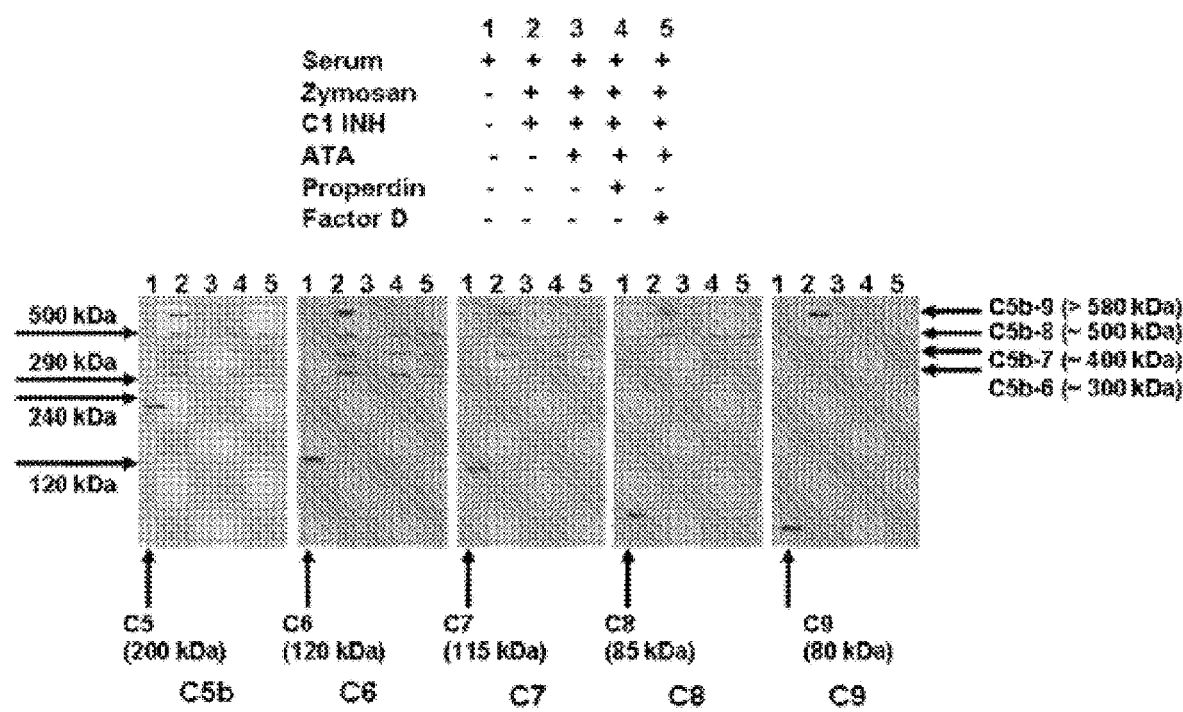

FIG. 5C shows the effects of these treatments on erythrocyte membranes developed with antibodies to the MAC components C5/C5b, C6, C7, C8 and C9. Lane 1 shows that bands for C5, C6, C7, C8 and C9 were readily detected in untreated serum. Lane 2 of membranes following serum treatment with zymosan and C1 inhibitor, resulted in disappearance of each of the protein bands and appearance of the MAC formation components C5b6, C5b67, C5b678, and the fully formed C5b-9. Lane 3 in which ATA was added shows that complete blockade appeared with no activation bands appearing on the membranes. Lanes 4 and 5, where the serum was supplemented with properdin and Factor D respectively, demonstrated partial activation of the complement system with weaker bands for C5b6, C5b67, and C5b678 appearing, but there was still blockade at the C5b-9 stage indicating that ATA was also blocking the addition of C9 to C5b-8.

Figure 6:
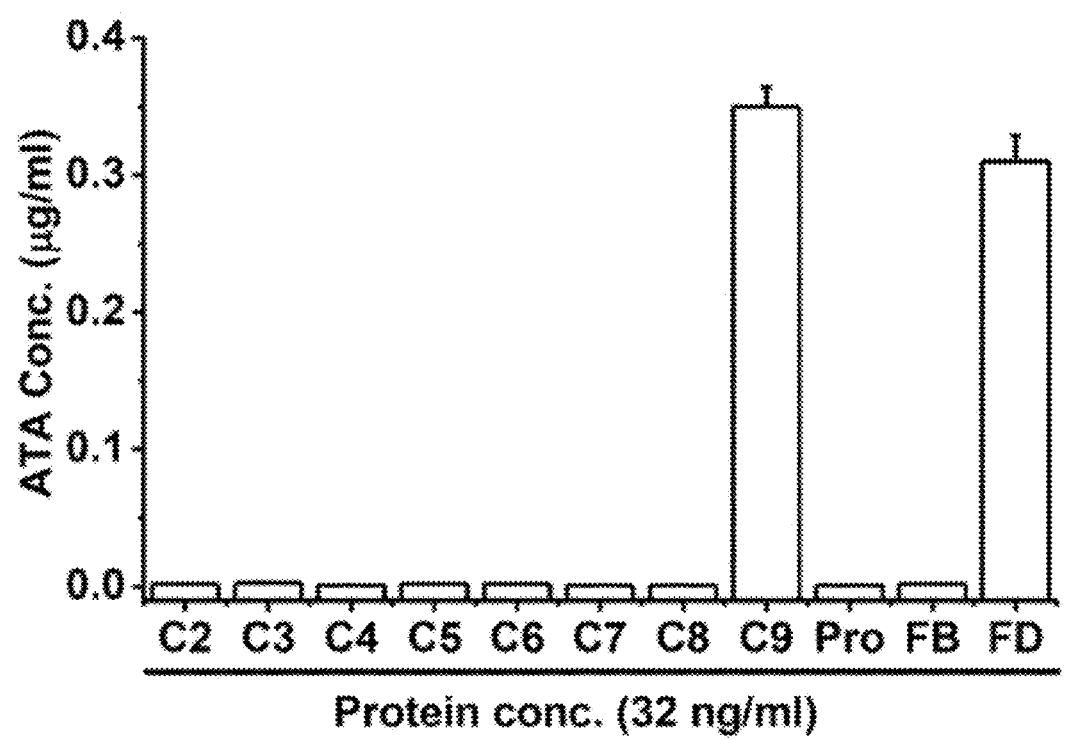
FIG. 6 is a diagram showing the binding of ATA to Factor D and C9, but not to properdin, factor B, C2, C3, C4, C5, C6, C7, or C8. These proteins were applied to microwell plates in concentrations of 1-32 ng/mL, following which ATA at 100 micrograms/mL was added.

The next set of experiments directly tested the binding of ATA to properdin, Factor D and complement proteins. These proteins were immobilized on microwell plates in a concentration range of 1-32 ng/mL. ATA was then added at a concentration of 100 microgm/mL and the solution incubated as described in methods. ATA binding to the proteins was then assayed according to our previously published fluorometric method (Lee et al. 2011)). FIG. 6 shows the results. There was no binding of ATA to properdin. Only background fluorescence was observed. This result is consistent with observations that properdin binding to erythrocyte membranes is unaffected by ATA. But ATA bound to both Factor D and C9 in a concentration dependent manner. Such binding explains why ATA blocks the alternative pathway at the stage where Factor D cleaves PC3B to form PC3Bb, and both the classical and alternative pathways at the stage where C9 adds to C5b678. However, other complement proteins such as C2, C3, C4, C5, C6, C7, C8 and Factor B (32 ng/mL each) did not bind with ATA.

Figure 7:
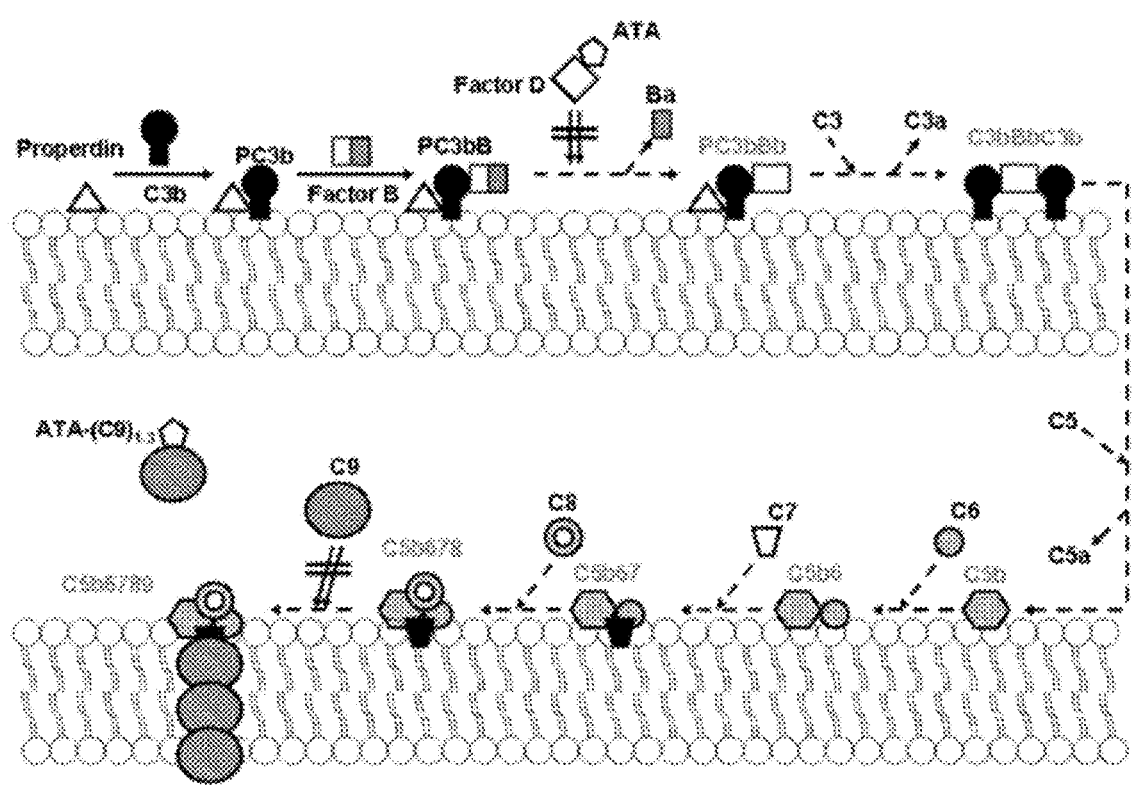
FIG. 7 is a schematic diagram of the alternative complement pathway illustrating blockade by ATA at the C3 convertase and C9 addition to C5b-8 stages.

In summary, FIG. 7 is a diagram of the alternative complement pathway showing the steps where ATA interferes. Activation of the alternative pathway first requires properdin binding to a target on the membrane. C3b can then attach to the bound properdin. Subsequently Factor B can be added. The critical stage is cleavage of Factor B on that complex to form C3 convertase (PC3bBb). Only then can significant amounts of C3 still remaining in the serum be cleaved and joined to C3 convertase to form C5 convertase (PC3bBbC3b). Factor D carries out this cleavage of Factor B. Since no bands incorporating Factor D were observed on Western blots of erythrocyte membranes, Factor D in the serum is unlikely to form a stable bond with membrane bound PC3bB. It may briefly attach to and cleave bound Factor B, then dissociating and returning to the serum along with Factor Ba. ATA interferes at this step, perhaps by binding to Factor D in solution preventing its access to bound PC3bB. If this step is overcome, so that C5 convertase can form (PC3bBbC3b), then ATA still blocks the addition of C9 to C5b678, preventing formation of the MAC. Thus ATA provides a two-step inhibition of the alternative pathway and may be particularly efficacious in conditions where unwanted activation of the alternative pathway occurs.

Synthesis and Filtration of ATA-Methylester

Figure 8:
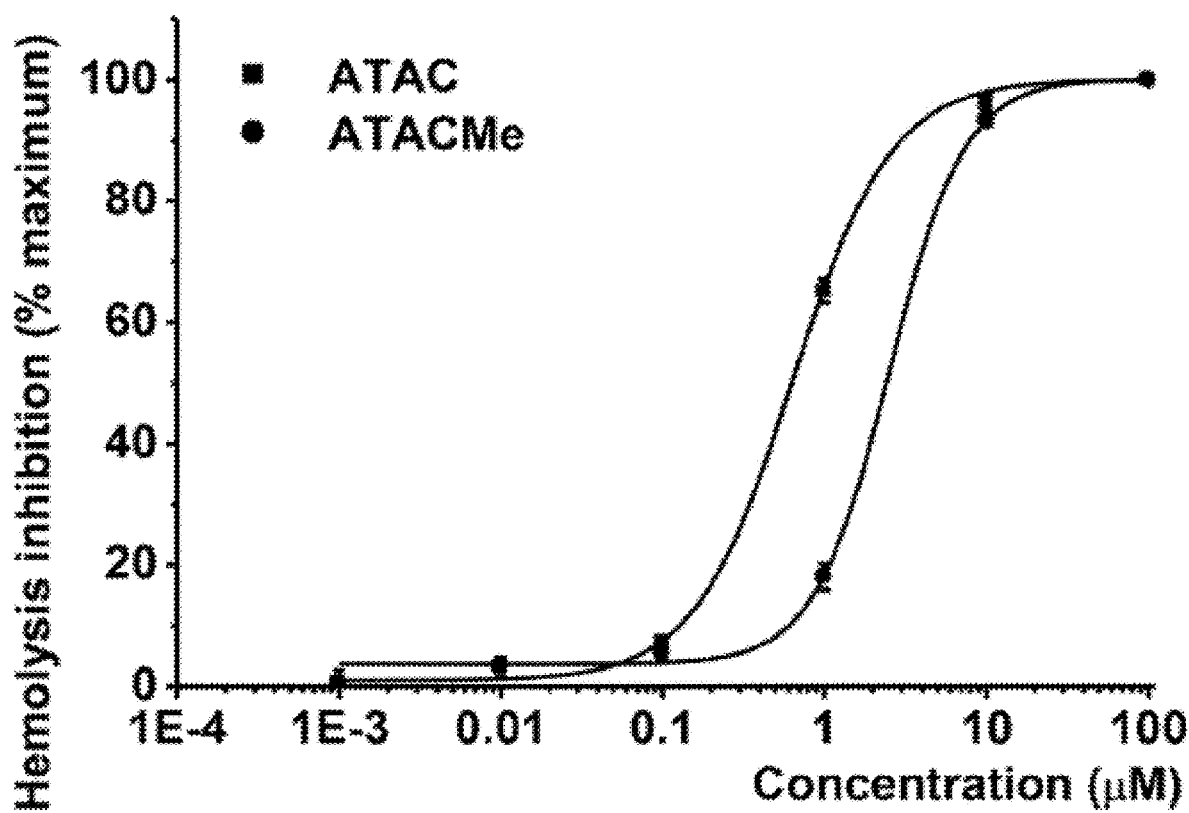
FIG. 8 shows a comparison of C1-150 results in human serum of ATAC and the methyl derivatives of ATAC. The methyl derivatives were less effective than ATA with an estimated IC50 of 2.52 microM.

To illustrate that simple derivatives of ATAC also have complement inhibiting properties, the methyl ester was synthesized and tested by the CH50 assay on human serum. Briefly, ATAC (0.8 g) was dissolved in methanol (16 mL). Concentrated sulfuric acid (610 microliters) was added. The reaction mixture was refluxed at 55° C. for 1 h. The solvent was evaporated and the remaining solid collected. The product was tested in a CH50 assay compared with the non-esterified material and was found to be 29% as active (FIG. 8, IC50 0.64 microM vs 2.52 microM assuming a MW of 422).

Applicability of the Invention to the Treatment of Human Disease.

General Considerations

The complement system has usually been interpreted as serving only the adaptive immune system. But it is also a mainstay of the innate immune system. It is called into play in all chronic degenerative diseases. If it is activated to the extent that the MAC is formed, there is danger of the pathology being exacerbated through bystander lysis. Damage can also occur by chronic activation of the alternative complement pathway. Therapeutic opportunities for intervention in a spectrum of human disease states have never been explored because there has never been previously described an orally effective complement inhibitor which is selective for blocking the MAC and alternative pathway activation. The invention described here illustrates examples of diseases where benefit in common degenerative diseases can be expected from utilization of the invention described here.

Rheumatoid Arthritis

There is strong evidence that both the classical and alternative pathways of complement are pathologically activated in rheumatoid arthritis (Okroj et al. 2007). The arthritic joint contains proteins capable of activating complement as well as proteins signifying that both the classical and alternative pathways have been activated. In mouse models of rheumatoid arthritis, resistance can be achieved by deletion of C3, C5, or factor B (Okroj et al. 2007). These data indicate that ATA or ATAC should be effective in rheumatoid arthritis.

Multiple Sclerosis

Multiple sclerosis is a relapsing-remitting disease characterized by inflammation of the white matter of brain. Specific antibodies have been detected which target myelin antigens indicating that it is an autoimmune disorder (Genain et al. 1999). Complement will be activated in this process indicating the appropriateness of ATAC therapy.

Malaria Infection

Malaria is a prevalent disease in Africa and south East Asia, resulting in an estimated 650,000 deaths per year. The infective agent, *plasmodium falciparum*, transmitted by mosquitos, produces enhanced complement activation in humans and susceptible animals. IgG and C3bBb complexes have been identified on erythrocytes of infected humans indicating damage caused by activation of both the classical and alternative pathways (Silver et al. 2010). Accordingly, treatment with ATAC should have beneficial effects.

Paroxysmal Nocturnal Hemoglobinemia

Paroxysmal nocturnal hemoglobinemia results from a clonal deficiency in erythrocytes of the X chromosome gene PIGA. As a consequence, the glycosal phophatidylinosotol moiety necessary for anchoring membrane proteins such as CD 55 and CD 59 is non functional. Erythrocytes and platelets lack the capacity to restrict cell-surface activation of the alternative pathway. Patients are subject to fatal thrombotic and hemolytic attacks. A treatment which is partially effective is to administer at biweekly intervals the monoclonal antibody eculizumab, which blocks C5 cleavage, preventing synthesis of the membrane attack complex. However this treatment is less than satisfactory being effective in only 49% of patients (Hillmen et al. 2006). A probable reason is that it does not block C3 convertase activity. C3 convertase is unregulated due to the CD 55 deficiency (Parker 2010). ATAC, because it is orally effective and compensates for both deficiencies, should be a truly definitive treatment for paroxysmal nocturnal hemoglobinemia.

Alzheimer's Disease

It has long been known that beta amyloid protein deposits in brain, which are believed to be the primary cause of the disease, can be identified by the opsonizing components of complement. It was demonstrated that this was due to C1q binding to beta amyloid protein (Rogers et al., 1992). It was also demonstrated that the membrane attack complex of complement decorated damaged neurites in the vicinity of the deposits, indicating self damage by the complement system (McGeer et al., 1989). Taken together, these data illustrate that the opsonizing aspects of complement need to be preserved so that phagocytosis of the beta amyloid deposits can occur, while the membrane attack complex needs to be selectively blocked so that self damage to host neurons can be eliminated.

Alzheimer's Disease—Testing in Mice

Since the invention requires material that can be safely administered on a continuing basis, it requires testing in vivo in animals. This can be achieved by feeding to mice or other species, a mixture of the powder obtained added to their normal chow. Our example was with mice that are transgenic for Alzheimer disease mutations (B6SJL-Tg). By employing such mice, the product was tested not only for safety, but also for potential efficacy in Alzheimer disease.

Control B6SJL-Tg mice were fed normal chow, and test B6SJL-Tg mice were fed show supplemented with 0.5 mg/kg ATAC. Based on chow consumption, it was calculated that test mice were receiving 5 mg/kg/day of ATAC. Feeding was started at ages from 56-63 days and was continued for a further 30 days or 48 days before sacrifice. Upon autopsy, no evidence of pathology in any organ of either the ATAC fortified or normal chow fed mice was observed. These data indicate that ATAC is well tolerated and apparently safe when continuously consumed at a dose of 5 mg/kg/day for 44 days.

Figure 9:
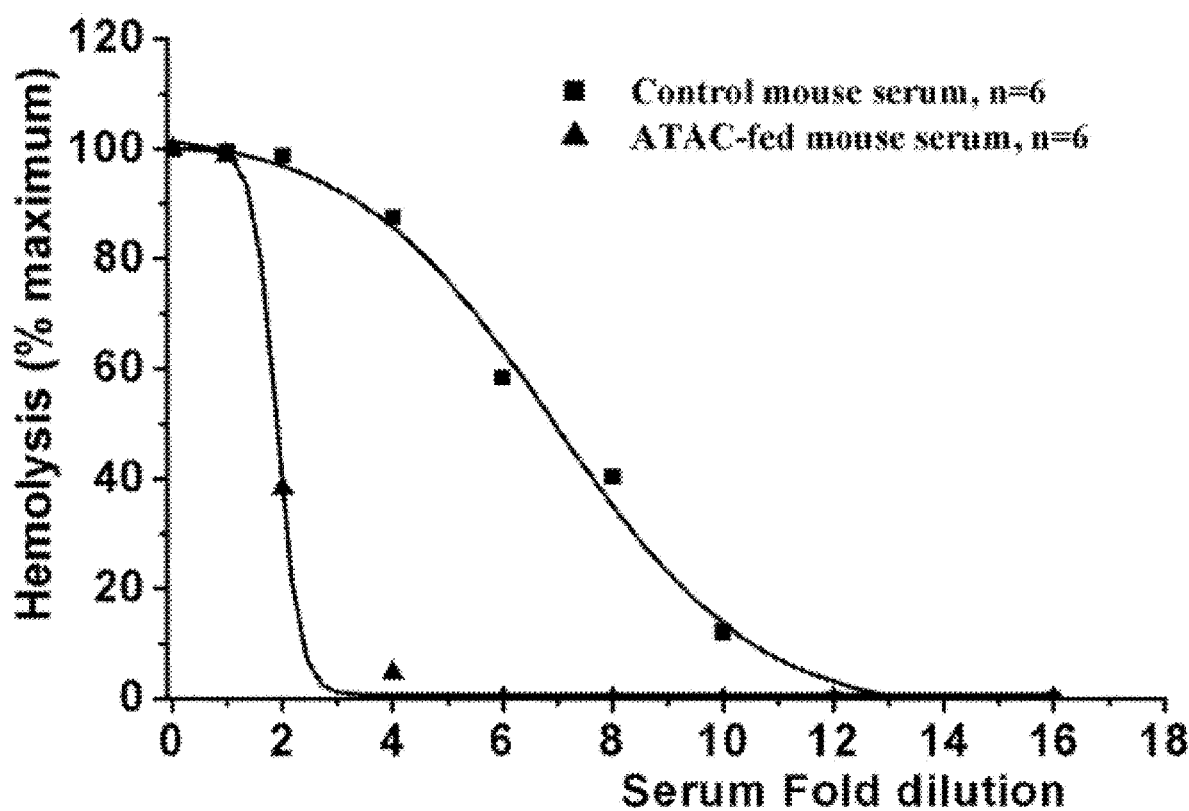
FIG. 9 shows the effects of orally administered ATAC on complement activation of mouse serum. Serum from six B6SJL-Tg mice fed normal chow was combined and compared with the combined serum from six B6SJL-Tg mice fed ATAC supplemented chow. The sera were subjected to 1-16 fold dilutions. The solutions (25 microliters) were incubated with 100 microliters of antibody-conjugated sheep red blood cells (5×106 cells) for 1 h. The mixtures were centrifuged, and the relative amount of hemoglobin released into 100 microliters of supernatant recorded by the absorbance at 405 nanometers. Serum from mice fed normal chow required more dilution than ATAC-fed mice for hemolysis to occur. The IC50s were 6.89 and 1.92 fold respectively corresponding to a 3.59 fold protection.

The results of CH50 assays are shown in FIG. 9. Serum at various dilutions (1-16 fold) was incubated with antibody-conjugated sheep red blood cells for 1 h. Serum from the fed mice required less dilution, consistent with inhibition of the membrane attack complex (IC50 1.92 fold vs. 6.89 fold for mice fed normal chow). These data indicate that a 3.59 fold protection was achieved. They establish that ATAC is absorbed after oral administration, and, at the doses tested, is an effective inhibitor of MAC formation.

Figure 10:
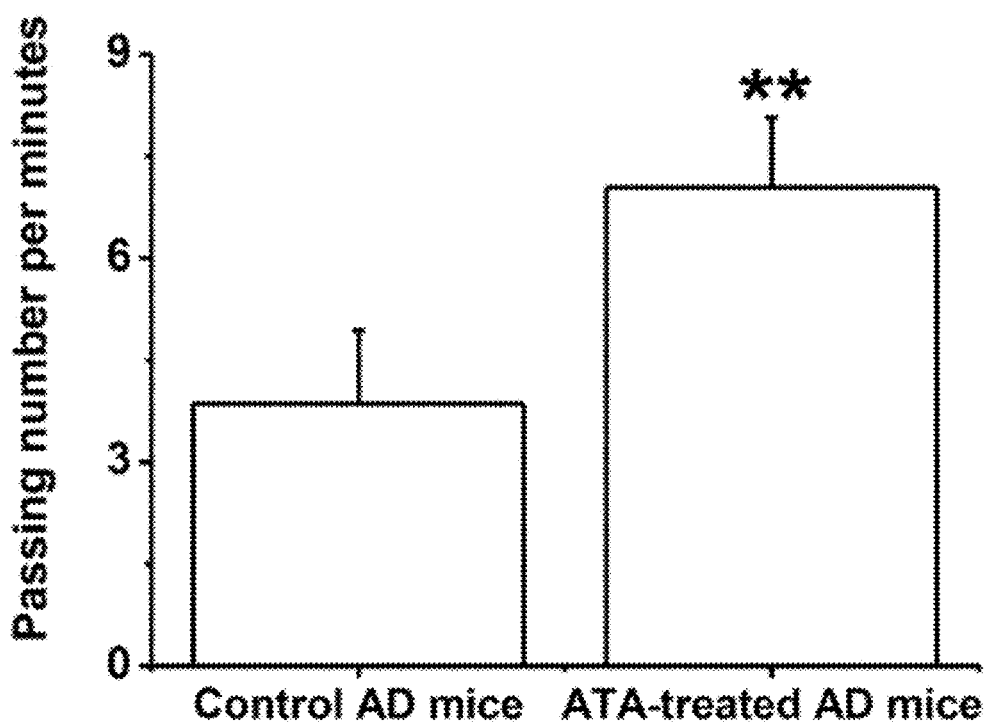
FIG. 10 shows memory retention of ATAC fed B6SJL-Tg mice compared with normal chow fed B6SJL-Tg mice as assessed by the rate of searching in the vicinity of the hidden platform after its removal on day 6 of testing. ATAC fed mice showed a significantly greater time searching in the correct area of the missing platform than mice fed normal chow, indicating a better retention of memory.

B6SJL-Tg mice develop early memory deficits due to the rapid buildup of beta amyloid protein deposits. The memory of B6SJL-Tg mice fed normal or ATAC chow was tested using a standard water maze test. It was performed in a pool of 1.5 meter diameter with opaque fluid and a 10 cm diameter hidden platform. Mice were placed in the pool for first-day visible training, followed by four days of training where the platform was hidden. The next day they were measured with the hidden platform removed to determine how quickly they returned to where the hidden platform had been placed and thus how well they remembered its location. The tracking of animal movements in the area where the platform had been located was captured by an HVS2020 plus image analyzer. Data were analyzed by two-way ANOVA. It was found that ATAC treated mice performed 2.5 fold better than the untreated mice. The data are shown in FIG. 10. In summary, these in vivo data on Alzheimer disease transgenic mice show that ATAC is not only safe, but beneficial in these animals. It improves weight gain and memory retention, which correlates with its ability to inhibit formation of the membrane attack complex of complement.

Age-Related Macular Degeneration

An estimated 10 million people in the United States and 50 million people worldwide suffer from age-related macular degeneration (AMD). There is currently no approved treatment that will prevent or arrest progression of this disease. It is characterized by degeneration of retinal pigment epithelial (RPE) cells. This is believed to result in destruction of photo receptor cells that are concentrated in the macula. AMD occurs in a dry form and a more serious wet form. In the dry form, drusen deposits are typically found throughout the retina. Since this occurs in many people with normal vision, drusen by themselves cannot be considered a cause. The wet form is a complication of the dry form, where new blood vessels, originating in the choroid, penetrate the retina. This neovascularization is associated with enhanced production of vascular endothelial growth factor (VEGF), but the stimulus for such production is unknown. Some slowing of the wet form has been achieved by direct injection of anti-VEGF monoclonal antibodies into the vitreous of the eye.

Age-Related Macular Degeneration—Testing in Mice

Rodents may be prone to the development of retinal pathology similar to that observed in human age related macular degeneration (AMD). Accordingly, the inhibitory effect of ATAC on deposition of the MAC in mouse retina was tested. Adult C57BL/6 mice (Charles River Laboratory, Wilmington Mass.) were divided into three groups: controls who received a single subcutaneous injection of sterile saline (N=2); a low dose ATAC group that received a single subcutaneous injection of 200 mg/kg (N=2); and a high dose ATAC group that received a single subcutaneous injection of 500 mg/kg (N=2). Mice were euthanized at 24 hours post injection. The eyes were enucleated, fixed in 4% paraformaldehyde, and paraffin embedded. Blood was harvested, the serum separated by centrifugation, and then frozen until utilized.

Figure 11A:
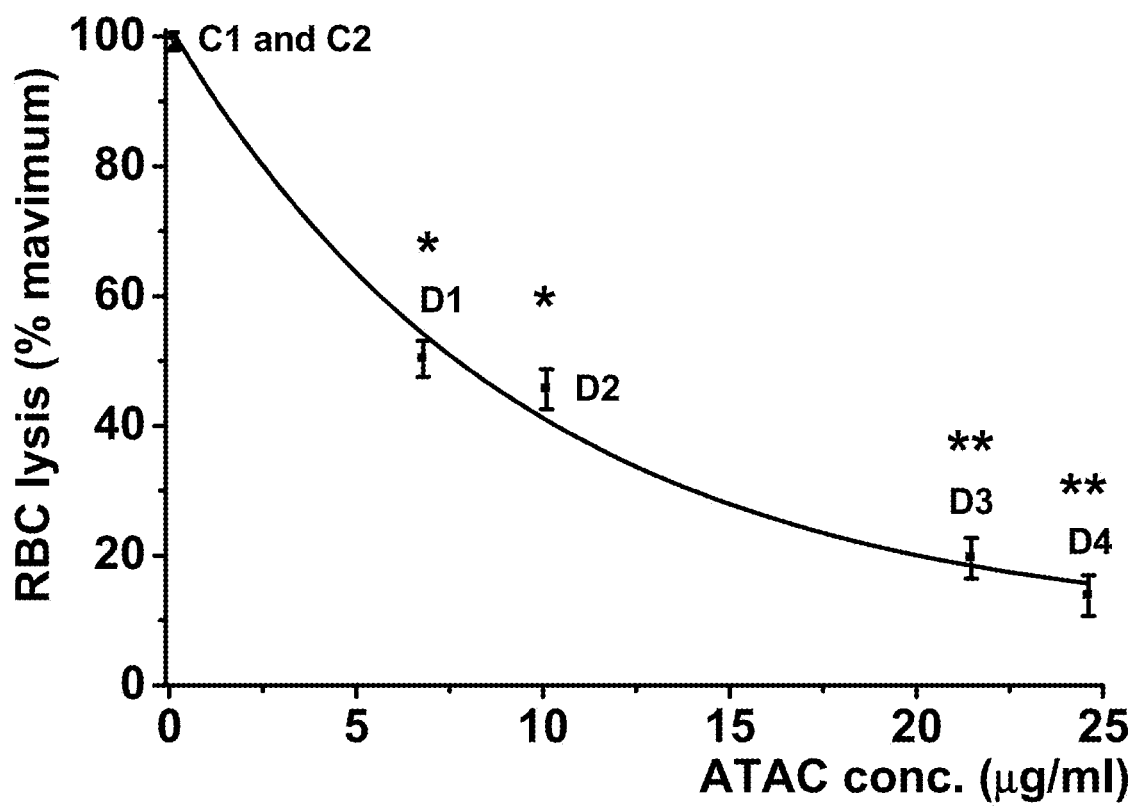
FIG. 11A is a graph showing concentration-dependent inhibition of ATAC against RBC lysis by zymosan-activated mouse complement. Values are mean±SEM, n=3 independent experiments. Two-way ANOVAs tests were carried out to test significance. Multiple group comparisons were followed by a post-hoc Bonferroni test where necessary. * P<0.01 compared with C1 or C2 groups and ** P<0.01 compared with D1 or D2 groups.

Serum ATAC levels were measured by a fluorescence method. To 100 µl of serum, 100 µl of isobutanol and 200 µl of 20% trichloroacetic acid were added. The mixture was centrifuged at 10,000 rpm for 5 min to remove the precipitated proteins. The supernatant was collected for fluorescence spectroscopy. The quantity of ATAC in the isobutanol supernatant was measured using a fluorescence spectrophotometer (Eclipse, Varian ISS, Chicago Ill.). The maximum absorption wavelength was 310 nanometers and the maximum emission wavelength was 450 nanometers. Standards were obtained by adding known amounts of ATAC to control serum. The C1 and C2 control mice showed only background levels of fluorescence. The D1 and D2 low dose mice showed levels of 6.8 and 10.1 micrograms/mL of serum respectively. The D3 and D4 high dose mice showed levels of 21.5 and 26.4 micrograms/mL of serum respectively. The ability of these sera to inhibit sheep red blood cell lysis in our standard CH50 assay was then tested. The complement system in serum was activated by zymogen and hemolysis measured by hemoglobin release. The results are illustrated in FIG. 11A. Maximum release of hemoglobin (100%) was that observed using control sera where no ATAC was present. A concentration-dependent inhibition was found for ATAC treated mice. D1 inhibited 50.3% (6.8 µg/mL); D2 inhibited 45.6% (10.1 µg/mL); D3 inhibited 19.6% (21.5 µg/mL); and D4 inhibited 13.8% (26.4 µg/mL).

Figure 11B:
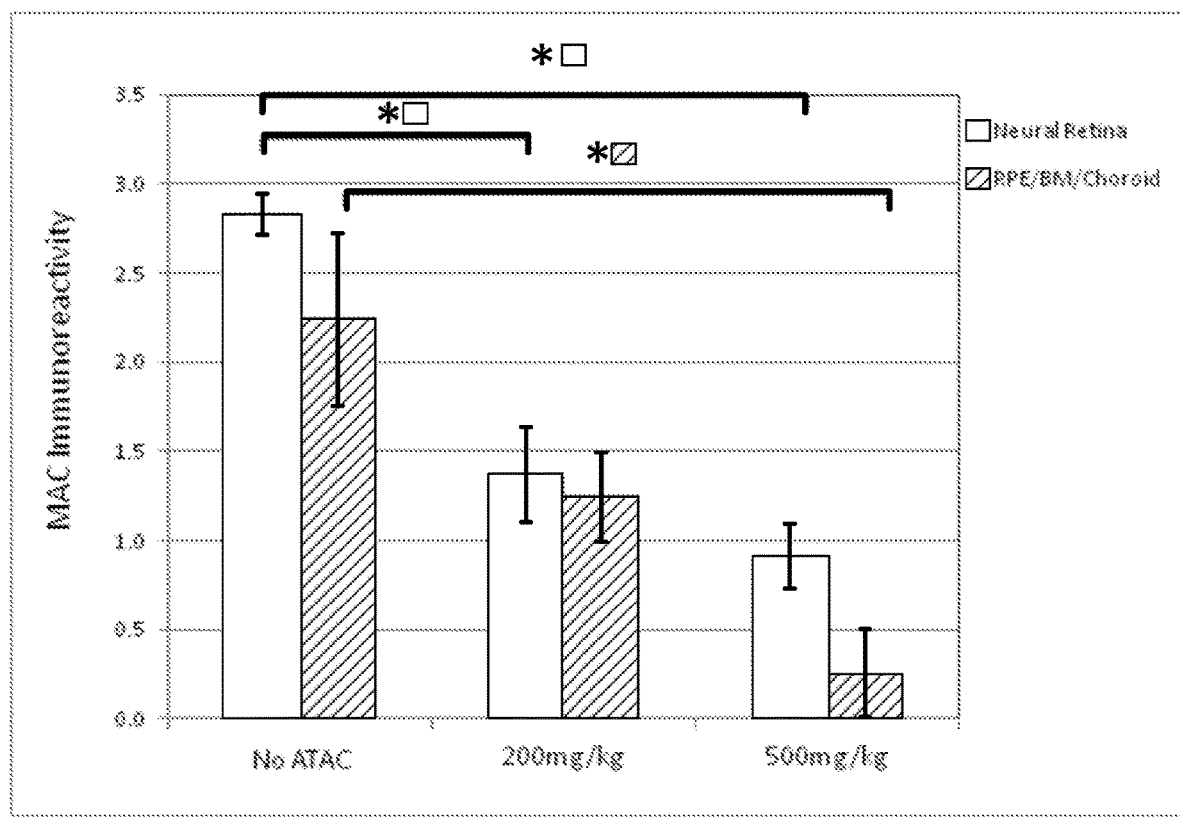
FIG. 11B is a graph showing semi-quantitative analysis of MAC immunoreactivity in mouse retina. The lefthand bar of each pair represents the mean score for neuroretinal layers, while righthand bar of each pair represents mean score for RPE/BM/choroid complex; error bars represent SEM. Significant difference was observed between untreated and 200 mg/kg ATAC for neuroretina, as well as untreated and 500 mg/kg ATAC for both neuroretina and RPE/BM/choroid complex. Mann Whitney U test was set for significance at *p<0.05. RPE, retinal pigment epithelium; BM, Bruch's Membrane.

The corresponding effect of complement activation on the retina is shown in FIG. 11B.

Sections containing the optic nerve head were treated with a polyclonal rabbit antibody (anti-05b-9, 1:500, Bloss, Woburn, Mass.) followed by a biotinylated secondary antibody. C5b-9 immunoreactivity was developed with Elite® ABC followed by Vector® VIP Substrate kits (Vector Laboratories, Burlingame, Calif.). Sections were counterstained with Methyl Green (Vector Laboratories, Burlingame, Calif.) and coverslipped.

MAC immunoreactivity was scored on a 0-3 point scaled using a 60× objective lens and 10× eyepieces on the neuroretina which included the ganglion cell, inner nuclear and outer nuclear layers, as well as the retinal pigmental epithelium/Bruch's membrane/choroid complex (RPE/BM/choroid complex).

ATAC treatments in mice significantly reduced neural retinal MAC immunoreactivity from 2.9 in the control group to 1.4±0.93 in the 200 mg/kg group and to 1.3±0.61 in the 500 mg/kg group. MAC levels were also significantly lower in the RPE/BM/choroid of mice in both treatment groups compared to the untreated group (FIG. 11B).

These data demonstrate that ATAC inhibits the ability of complement activated serum to attack and damage the neural retina and RPE/BM/Choroid in mice. It provides evidence that ATAC will be beneficial in treating human AMD.

Age-Related Macular Degeneration—Testing in Human Patient

The present inventors tested the hypothesis that administration of ATAC might be a helpful way to treat AMD generally by inhibiting formation of the MAC.

A female patient age 79 with longstanding wet AMD in both eyes was provided with ATAC. She had previously had 6 surgeries on her left eye with almost complete loss of eyesight in that eye. She also suffered from a debilitating stabbing nerve pain in that eye. After taking 500 mg of ATAC orally per day for 14 days, the severe pain was greatly diminished. She also noticed slight return of light-dark vision in that eye. She went off ATAC after 14 days and within a week the pain returned and the gain in vision was lost.

The patient resumed taking ATAC and, except for a 2-month interlude in hospital, has been doing so for the past year. For a 4 month period she received intraocular injections of the drug EYLEA™ in the right eye which was stopped after retinal bleeding stopped. With each visit to a retinal specialist her vision showed improvement. However she had a fall, became hospitalized for 2 months, and was unable to continue ATAC in the hospital. Upon release, the retinal specialist noted her vision had badly deteriorated. She resumed treatment with ATAC and her improvement has been regained. These data indicate that ATAC can arrest progression of wet AMD and can bring about at least modest improvements in vision.

Atherosclerosis

Atherosclerosis has not generally been considered to be exacerbated by the complement system. However the mRNA for C-reactive protein, a known activator of complement, is upregulated more than ten fold in the area of atherosclerotic plaques. Plaque areas showing upregulation of C-reactive protein and the opsonization components of complement also demonstrate presence of the membrane attack complex (Yasojima et al., 2001). This is a further example of a common human degenerative condition where the membrane attack complex is present in a sterile situation and can therefore only damage host tissue. Again, the invention described here will preserve the desirable phagocytosis stimulating aspect of complement, while eliminating the self damaging aspect of the membrane attack complex.

Atypical Hemolytic Uremia Syndrome

Atypical hemolytic uremia syndrome (aHUS) is a life threatening kidney disease. The present inventors tested the hypothesis that administration of ATAC might be a helpful way to treat aHUS.

Atypical Hemolytic Uremia Syndrome—Testing in Human Blood Sample

The present inventors tested the efficacy of ATAC against aHUS. A middle aged male, known to have been suffering from aHUS for many years, provided a blood sample for testing. He had previously been treated by plasma exchange, and had been receiving biweekly infusions of eculizumab for several months. The blood sample was centrifuged to separate the red blood cells (RBCs) from the serum. The patient's RBC's were then compared with normal RBCs in our standard CH50 assay [(Lee M, McGeer P L (2014). In this assay, serum is activated with zymosan and its ability to hemolyse RBCs measured. It was found that the patient's RBCs were approximately 25% more vulnerable to serum complement attack than normal RBCs. ATAC, added to the serum at a concentration of approximately 3 micrograms per mL, restored the resistance of patient's RBCs to hemolysis to that of normal RBCs. These data establish that ATAC will be an effective treatment for aHUS.

As those skilled in the art will know, these diseases are only examples of many that may be found where the invention described here will have therapeutic benefit. This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

REFERENCES CITED

Patent Documents

McGeer et al. U.S. patent application Ser. No. 13/195,216 filed Aug. 1, 2011.
Bernstein et al. U.S. Pat. No. 4,007,290 issued Feb. 8, 1977.

OTHER PUBLICATIONS

Anderson D. H., Mullins R. F., Hageman G. S., Johnson L. V., 2002. A role for local inflammation in the formation of drusen in the aging eye. Am. J. Ophthalmol. 134(3): 411-431.

Anderson D. H., Radeke M. J., Gallo N. B., Chapin E. A., Johnson P. T., Curlettie C. R., Hancox L. S., Hu J., Ebright J. N., Malek G., Hauser M. A., Rickman C. B., Bok D., Hageman G. S., Johnson L. V., 2010, The pivotal role of the complement system m aging and age-related macular degeneration; hypothesis revisited. Prog. Ret. Eve Res. 29: 95-112.

Cushman M., Kanamathareddy S., 1990. Synthesis of the covalent hydrate of the incorrectly assumed structure of aurintricarboxylic acid. Tetrahedron 46(5): 1491-1498.

Cushman M., Kananathareddy S., De Clercq E., Scols D., Goldman M. E., Bowen J. A., 1991. Synthesis and anti-HIV activities of low molecular weight aurintricarboxylic acid fragments and related compounds. J. Med. Chem 34: 337-342.

Cushman M., Wang P., Stowell J. G., Schols D., De Clercq E., 1992. Structural investigation and anti-HIV activities of high molecular weight ATA polymers. J. Org. Chem. 57: 7241-7248.

Genain C. P, Cannelloa B., Hauser S. I., et al., 1999. Identification of autoantibodies associated with myelin damage in multiple sclerosis. Nat. Med. 5, 170-175.

Gonzalez R. C., Blackburn B. J., Schleich T., 1979. Fractionation and structural elucidation of the active components of aurintricarboxylic acid, a potent inhibitor of protein nucleic acid interactions. Biochimica et Biophysica Acta 562: 534-545.

Heisig G. B., Lauer M., 1941. Ammonium salt of aurin tricarboxylic acid. Organic Syntheses 1: 54.

Hillmen, P., Young, Schubert, J., et al., 2006. The complement inhibitor eculizumab in paroxysmal nocturnal hemoglobinuria. N. Engl. J. Med. 355, 1233-1243.

Kira S., Ihara K., Takada H., Gondo K., Hara T., 1998. Nonsense mutation in exon 4 of human complement C9 gene is the major cause of Japanese complement C9 deficiency. Human Gen. 102(6): 605-610.

Lee, M., Guo, J. P., Schwab, C., McGeer, E. G., and McGeer, P. L., 2012. Selective inhibition of the membrane attack complex of complement by low molecular weight components of the aurin tricarboxylic acid synthetic complex. Neurobiol. Aging. doi: http://dx.doi.org/10.1016/j.neurobiolaging.2011.12.005.

Lee, M., Narayanan, S., McGeer, E. G., and McGeer, P. L., 2014. Aurin tricarboxylic acid protects against red blood cell hemolysis in patients with paroxysmal nocturnal hemoglobinemia. PLOS ONE http://www.plosone.org/article/info%3Adoi%2F10.1371%2Fjournal.pone.0087316

McGeer P. L., Akiyama H., Itagaki S., McGeer E. G., 1989. Activation of the classical complement pathway in brain tissue of Alzheimer patients. Neuroscience Letters 107: 341-346.

Okraj, M., Heinegard, D., Holmdahl, R., and Blom, A. M., 2007. Rheumatoid arthritis and the complement system. Ann. Med 39, 517-530.

Owens M. R., Holme S., 1996. Aurin tricarboxylic acid inhibits adhesion of platelets to subendothelium. Thrombosis Res. 81: 177-185.

Parker C J., 2012. Paroxysmal nocturnal hemoglobinuria 19(3):141-148.

Rogers J., Cooper N. R., Webster S., Schultz J., McGeer P. L., Styren S. D., Civin W. H., Brachova L., Bradt B., Ward P., Lieberburg I., 1992. Complement activation by b-amyloid in Alzheimer disease. 1992. Proc Natl Acad Sci USA 89:10016-10020.

Silver K. L., Higgins S. J., McDonald C. R., and Kain K. C., 2010. Complement driven immune responses to malaria: fuelline severe malarial diseases. Cellular Microbial. 8, 1036-1045.

Yasojima K., Schwab C., McGeer E G, McGeer P. L., 2001. Generation of C-reactive protein and complement components in atherosclerotic plaques. American J. Pathol. 158(3): 1039-1051.

The invention claimed is:

1. A method of treating age-related macular degeneration, the method comprising administering orally or parenterally an effective amount of aurin tricarboxylic acid, aurin quadracarboxylic acid, and/or aurin hexacarboxylic acid, wherein the method excludes administration of components of aurin tricarboxylic acid complex of greater than or equal to 1 kilodalton in molecular weight.

2. A method according to claim 1 wherein the condition being treated is wet age-related macular degeneration.

3. A method according to claim 2 wherein an effective amount of aurin tricarboxylic acid is administered.

4. A method according to claim 2 wherein an effective amount of aurin quadracarboxylic acid is administered.

5. A method according to claim 2 wherein an effective amount of aurin hexacarboxylic acid is administered.

6. A method according to claim 1 wherein the condition being treated is dry age-related macular degeneration.

7. A method according to claim 6 wherein an effective amount of aurin tricarboxylic acid is administered.

8. A method according to claim 6 wherein an effective amount of aurin quadracarboxylic acid is administered.

9. A method according to claim 6 wherein an effective amount of aurin hexacarboxylic acid is administered.

* * * * *